(12) United States Patent
Eaton et al.

(10) Patent No.: US 10,245,139 B2
(45) Date of Patent: Apr. 2, 2019

(54) APPARATUS AND METHOD FOR CLAMPING AND TRIMMING THE BONE TENDON OF A GRAFT TO A DESIRED SIZE

(71) Applicant: Koco Clamp, LLP, St. Petersburg, FL (US)

(72) Inventors: Katulle K. Eaton, St. Petersburg, FL (US); Jon R. Enerson, New Port Richey, FL (US)

(73) Assignee: KOCO CLAMP, LLP, St. Petersburg, FL (US)

( * ) Notice: Subject to any disclaimer, the term of this patent is extended or adjusted under 35 U.S.C. 154(b) by 0 days.

(21) Appl. No.: 15/862,018

(22) Filed: Jan. 4, 2018

(65) Prior Publication Data

US 2018/0125637 A1    May 10, 2018

Related U.S. Application Data

(63) Continuation of application No. 14/825,626, filed on Aug. 13, 2015, now Pat. No. 9,872,761.

(60) Provisional application No. 62/036,942, filed on Aug. 13, 2014.

(51) Int. Cl.
*A61B 17/58* (2006.01)
*A61B 17/60* (2006.01)
*A61F 2/00* (2006.01)
*A61F 2/08* (2006.01)
*A61B 17/15* (2006.01)

(52) U.S. Cl.
CPC ............ *A61F 2/0805* (2013.01); *A61B 17/15* (2013.01)

(58) Field of Classification Search
None
See application file for complete search history.

(56) References Cited

U.S. PATENT DOCUMENTS

2012/0253350 A1* 10/2012 Anthony ................ A61B 17/14
606/87

* cited by examiner

*Primary Examiner* — Sameh Boles
(74) *Attorney, Agent, or Firm* — GrayRobinson, P.A.

(57) ABSTRACT

An instrument for clamping and trimming the bone tendon portion of a graft to a desired size, comprising a pair of elongated handles each having jaws at one end; the handles being hinged together at a pivot point allowing the jaws to open and close in a scissor arrangement, the jaws defining a generally U-shaped trapezoidal receptacle when the jaws are closed about the bone tendon portion of the graft to be trimmed and the jaws comprising respective upper guide surfaces along their upper edges whereby, when a bone tendon portion is positioned in the U-shaped trapezoidal receptacle, the upper guide surfaces function as a guide for a blade of a saw to trim any excess portion of the bone tendon portion protruding above the upper guide surfaces.

5 Claims, 58 Drawing Sheets

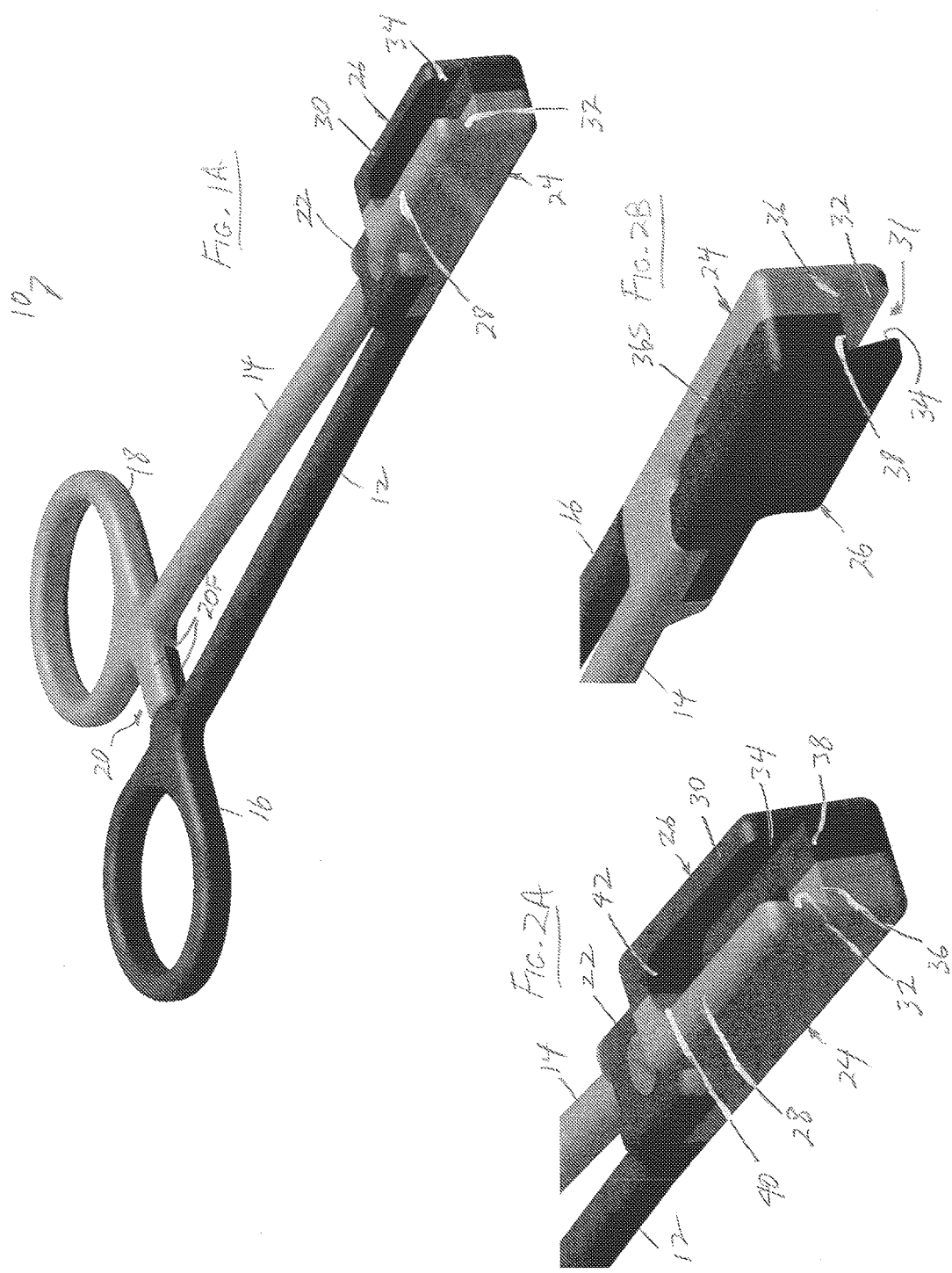

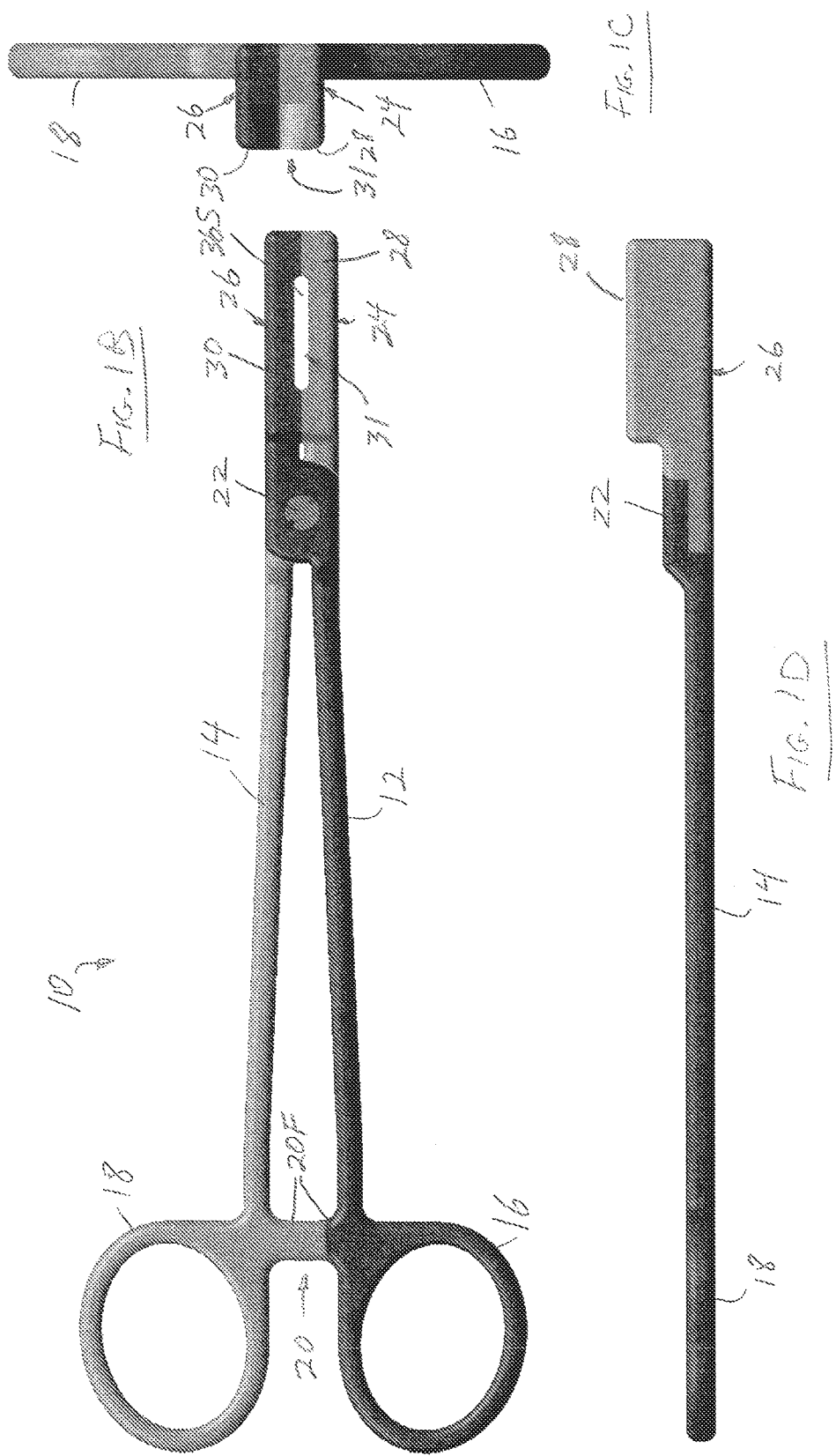

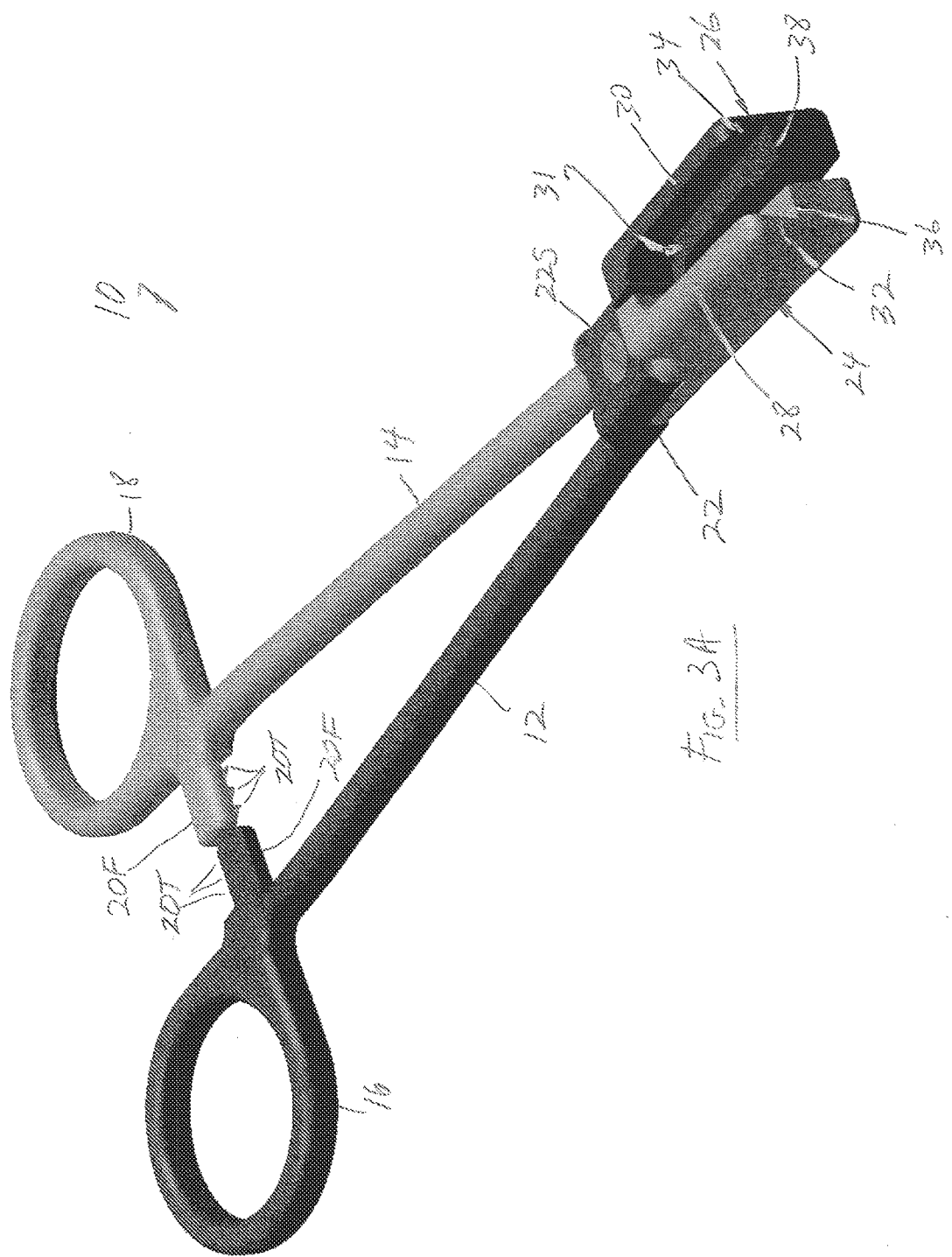

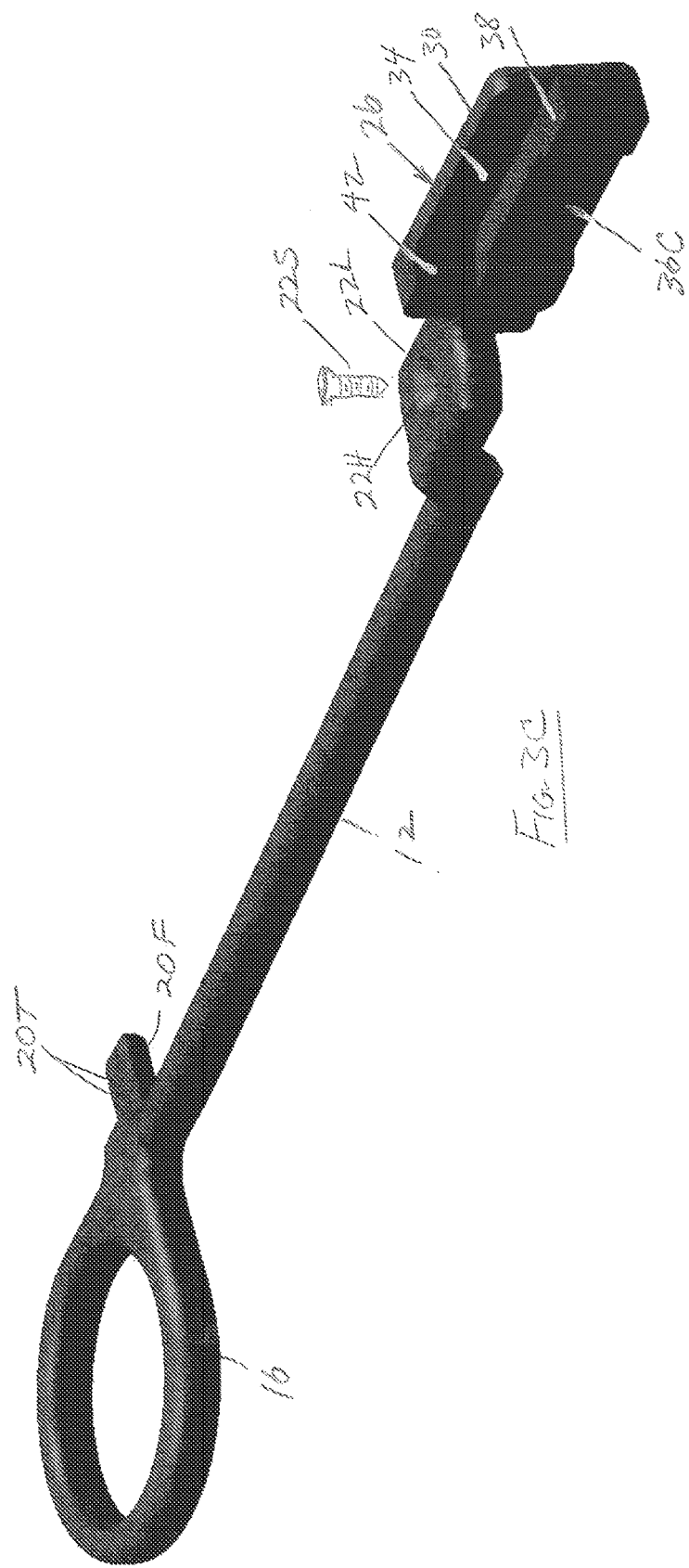

APPARATUS AND METHOD FOR CLAMPING AND TRIMMING THE BONE TENDON OF A GRAFT TO A DESIRED SIZE

CROSS REFERENCE TO RELATED APPLICATIONS

This application is a continuation of U.S. utility application Ser. No. 14/825,626, filed Aug. 13, 2015 which claims the benefit of U.S. provisional application 62/036,942, filed Aug. 13, 2014, the disclosures of which are hereby incorporated by reference herein.

BACKGROUND OF THE INVENTION

Field of the Invention

This invention relates to instruments used during surgical procedures for securing a bone tendon bone graft inside bone tunnel. More particularly, this invention relates to bone clamping instruments for trimming the bone tendon portion of a graft for a replacement anterior cruciate ligament (ACL) or other tendon/ligament.

Description of the Background Art

Presently there exist many surgical techniques employed for replacing, reconstructing or securing synthetic or biological connective tissues to bone surfaces, such as attaching and maintaining an anterior cruciate ligament (ACL) within a knee. More recent surgical procedures for tendon replacement and reconstruction involve auto-grafting a tendon to the site of a torn or dislocated tendon. Early surgical procedures involved stapling the auto-grafted tendon into placement.

More particularly, reconstruction is the standard of care after an ACL injury. In surgery it is generally known to use an autograft taken from the knee of the patient to replace the ruptured ACL. The two most commonly used are the bone-patellar tendon bone (BPTB) and the hamstring tendon (semitendinosus tendon with or without gracilis tendon). Allografts, synthetic grafts and quadriceps tendon grafts have also been used as ACL substitutes. The surgical techniques of the ACL reconstruction using bone-tendon bone (BTB) graft and hamstring tendon graft are described in detail in the following references: Beck, C. L., Jr.; Paulos, L. E.; Rosenberg, T. D.: "Anterior cruciate ligament reconstruction with the endoscopic technique," *Operative Techniques in Orthopaedics*, 2:96-98, 1992; Stahelin, A. C.; Weiler, A.: "All-inside anterior cruciate ligament reconstruction using semitendinosus tendon and soft threaded biodegradable interference screw fixation," *Arthroscopy*, 13:773-779, 1997; Fu, F. H.; Ma, C. B.: "Anterior Cruciate Ligament Reconstruction Using Quadruple Hamstring. Operative Techniques," *Orthopaedics*, 9:264-272, 1999. Additional references of interest include Hoffman, R. F. G.; Peine, R; Bail, H. J.; Sudkamp, N. P.; Weiler, A.: "Initial fixation strength of modified patellar tendon grafts for anatomic fixation in anterior cruciate ligament reconstruction," *Arthroscopy*, 15:392-399, 1999. The disclosures of each of the above references are hereby incorporated by reference herein.

More specifically, among the currently available soft tissue (hamstring) graft fixation implants, currently the most commonly used method to secure an ACL substitute to a bony drill-hole in an ACL reconstruction, is the interference technique. In the interference technique, an interference screw is inserted into the space between the drill-hole and the bone tendon portion of the graft to lock it into the drill-hole. The fixation screws, like interference screws, are normally made of metal, like stainless steel or titanium or of a bioabsorbable polymer, like polylactide.

For example, as taught by U.S. Pat. No. 5,397,356, one technique for securing a replacement tendon to a bone involves harvesting a tendon having a bony section or plug at one or both ends. The tendon is threaded into a drilled hole by a guide pin or K-wire and then the bone plug is secured into position by a specially-adapted threaded pin. Importantly, the threaded pin securing the replacement tendon engages through its bony plug to secure it into position within the hole whereupon, over time, the bony plug is grafted into the knee, thereby permanently securing the replacement tendon into position.

It is important to trim the bone tendon portion of the graft to properly fit inside the bony drill-hole. Unfortunately, prior art techniques have involved trimming the bone tendon portion with a bone saw by hand without the aid of an instrument and possibly resulting in incorrect sizing of the bone tendon portion either too large or too small to properly fit into the boney drill hole.

An object of this invention is to provide a bone clamping instrument for clamping the bone tendon portion of the graft during an ACL procedure allowing the surgeon to properly trim the bone tendon portion of the graft with a bone saw to precise dimensions to properly fit into the hole.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, this invention comprises a bone clamping instrument for clamping the bone tendon portion of the graft during an ACL procedure allowing the surgeon to properly trim the bone tendon portion of the graft with a bone saw to precise dimensions to properly fit into the hole. The instrument of the invention comprises a pair of jaws pivotally connected together in the form of a scissor arrangement with handles. The jaws, when closed, define a generally U-shaped trapezoidal receptacle to grasp the bone tendon portion of the graft. As the bone tendon portion is cradled between the jaws, the upper surfaces of the jaws provide a level bone-cutting surface allowing the surgeon, with the aid of a conventional bone saw, to trim off any portion of the bone tendon portion protruding from the top of the U-shaped trapezoidal receptacle. Once trimmed, the bone tendon will have a height equal to the depth of the U-shaped trapezoidal receptacle, thereby assuring that the bone tendon portion will be trimmed to properly fit into the boney hole.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIGS. 1A, 1B, 1C and 1D are perspective, top plan, right plan and front plan views, respectively, of the bone clamping instrument of the invention illustrating the generally U-shaped trapezoidal receptacle formed by the jaws of the instrument when closed;

FIGS. 2A and 2B are enlarged, partial perspective views of the generally U-shaped trapezoidal receptacle formed by the jaws of the instrument when closed;

FIG. 3A is a perspective view of the bone clamping instrument of the invention illustrating the generally U-shaped trapezoidal receptacle formed by the jaws of the instrument when partially opened;

FIGS. 3B and 3C are perspective views of the disassembled right and left handles, respectively, of the instrument showing the cut-outs formed along the bottom of the respective jaws to define a through-slot into which the drill bit may pass when drilling a hole into the bone tendon portion.

Similar reference characters refer to similar parts throughout the several views of the drawings.

DETAILED DESCRIPTION OF THE PREFERRED EMBODIMENT

Figure 3B:
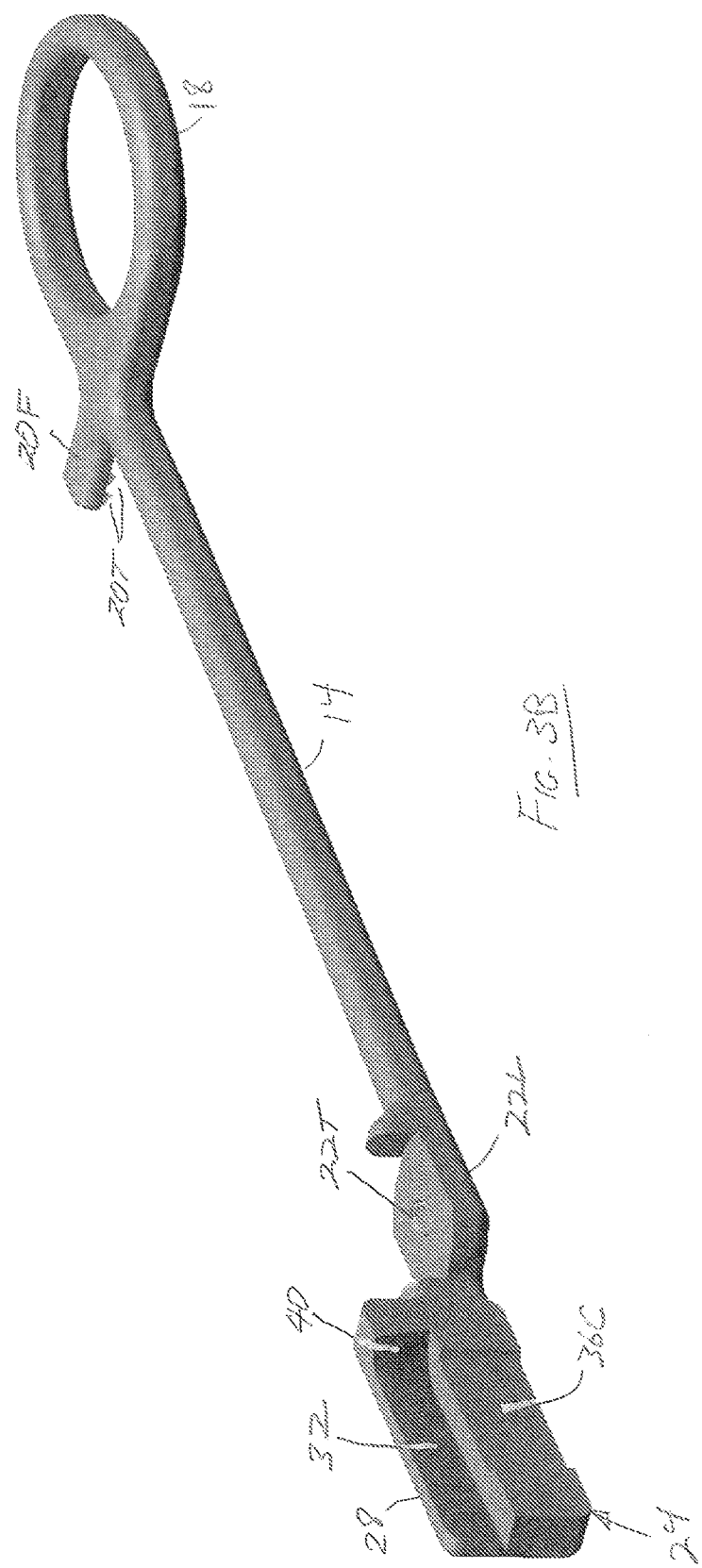

Referring to FIGS. 1A-1D, the bone clamp 10 of the invention comprises a pair of elongated handles 12 and 14 each having thumb/finger loops 16 and 18 at one end and jaws 24 and 26 at their other end. The handles 12 and 14 are hinged together at pivot point 22 allowing the jaws 24 and 26 to open and close in a scissor arrangement. The jaws 24 and 26 define a generally U-shaped trapezoidal receptacle 31 when the jaws 24 and 26 are closed (see FIG. 1C) to grasp the bone tendon portion of the graft to be trimmed. The jaws 24 and 26 comprise respective upper guide surfaces 28 and 30 along their upper edge. When a bone tendon portion is positioned in the trapezoidal receptacle 31, the upper guide surfaces 28 and 30 function as a guide for the blade of the bone saw to trim the excess portion of the bone tendon portion protruding above the upper surfaces 28 and 39.

A conventional clamp mechanism 20 releasably interconnects the handles 12 and 14. The clamp mechanism 20 comprises respective fingers 20F emanating from the handles 12 and 14, preferably at their loops 16 and 18. Each finger 20F comprises ratchet teeth 20T to engage the mating ratchet teeth 20T of the other finger 20F in a mating, progressively locking manner to progressively lock the jaws 24 and 26 as the jaws 24 and 26 are moved closed. The jaws 24 and 26 may then subsequently opened by twisting the handles 12 and 14 apart to disengage the ratchet teeth 20T.

As best shown in FIG. 3A, preferably the fingers 20F are dimensioned such that their respective outermost ratchet teeth 20T start to engage one another when the jaws 24 and 26 are about to close. Then, as the scissor arrangement fully closes, additional respective ratchet teeth 20T engage (compare the partially-closed FIG. 3A with the fully-closed FIG. 1A).

Referring to FIGS. 2A and 2B, the jaws 24 and 26 are configured as mirror images of one another (see also FIGS. 3B and 3C), having respective upstanding, inwardly-sloping sidewalls 32 and 34 (i.e., sloping from a narrower width at the top to a wider width at the bottom of the jaws 24 and 26 to define the generally U-shaped trapezoidal receptacle 31 when the jaws 24 and 26 are closed (see FIG. 1C) to grasp the bone tendon portion of the graft to be trimmed. The jaws 24 and 26 comprise respective upper bone saw upper guide surfaces 28 and 30 along their upper edges.

During use with the bone tendon portion of the graft cradled in the jaws 24 and 26 and the clamping mechanism 20 clamped together to hold the bone tendon portion therebetween, the surgeon may trim any excess of the bone tendon portion protruding above the upper guide surfaces 28 and 30 using a conventional bone saw by simply resting and moving the bone saw blade along the upper guide surfaces 28 and 30, thereby assuring that the bone tendon portion will have a fixed height equal to the depth of the U-shaped trapezoidal receptacle.

The process may then be repeated to trim along other side(s) of the bone tendon portion, by releasing the bone tendon portion from the jaws 24 and 26, rotating it to the side to be trimmed (e.g., ninety degrees), re-grasping it with the jaws 24 and 26 and then trimming the protruding excess of the bone tendon portion.

More particularly, as best shown in FIG. 1C, the transverse cross-sectional configuration of the generally U-shaped trapezoidal receptacle 31 is defined by the inwardly-sloping sidewalls 32 and 34 which function to securely grasp the bone tendon portion when clamped between the jaws 24 and 26. As best shown in FIGS. 2A, 3B and 3C, the length of the longitudinal cross-sectional configuration of the generally U-shaped trapezoidal receptacle 31 is defined by the length of the respective upstanding rear walls 40 and 42. The rear walls 40 and 42 are preferably arcuate shaped to define a generally rounded rear of the generally U-shaped trapezoidal receptacle 31.

As best shown in FIGS. 3B and 3C, the pivot point 22 comprises upper and lower generally flat leafs 22L that mate together and are secured in a pivoting arrangement by a pivot screw 22S engaged through a hole 22H formed in one leaf 22L into the threaded hole 22T of the other leaf 22L thereby forming a single-point pivot 22. The rear portions of the leafs 22L are connected to the front ends of the respective handles 10 and 12 whereas the front portions of the leafs 22L are connected to the rear portions of the respective jaws 24 and 26.

Referring now to FIGS. 3B and 3C showing the disassembled right and left handles 10 and 12, a cut-out 36C is formed along the mating sides of the respective bottoms 36 and 38 of the jaws 28 and 30. As shown in FIG. 1B, when the jaws 28 and 30 are closed, the mating cut-outs 36C define a through-slot 36S. The through-slot 36S allows space for the tip of the drill bit to pass into when drilling a hole into the bone tendon portion.

Figure 4:
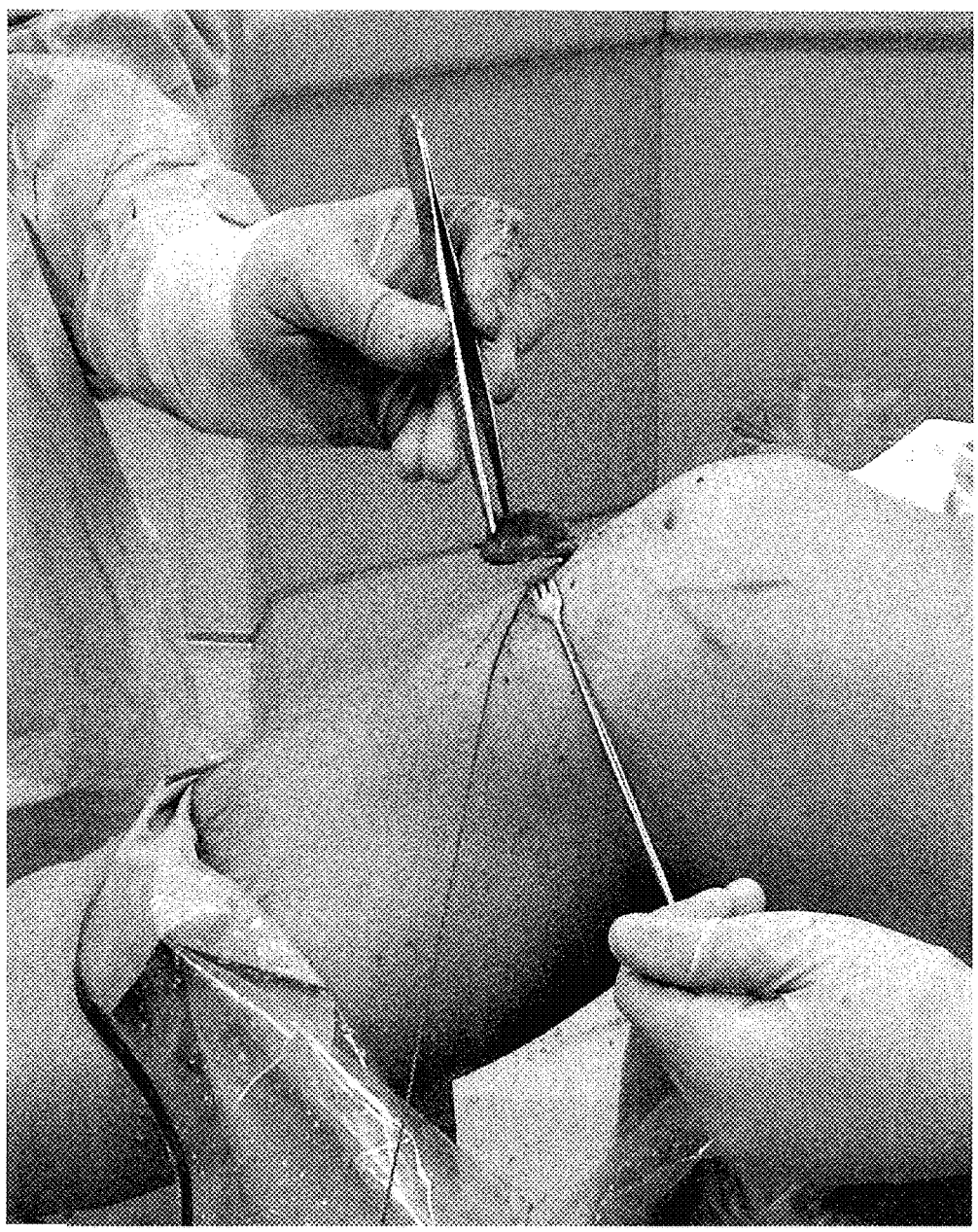
FIGS. 4-56 are photographs of a surgical ACL procedure utilizing the bone clamping instrument of the invention.
Figure 5:
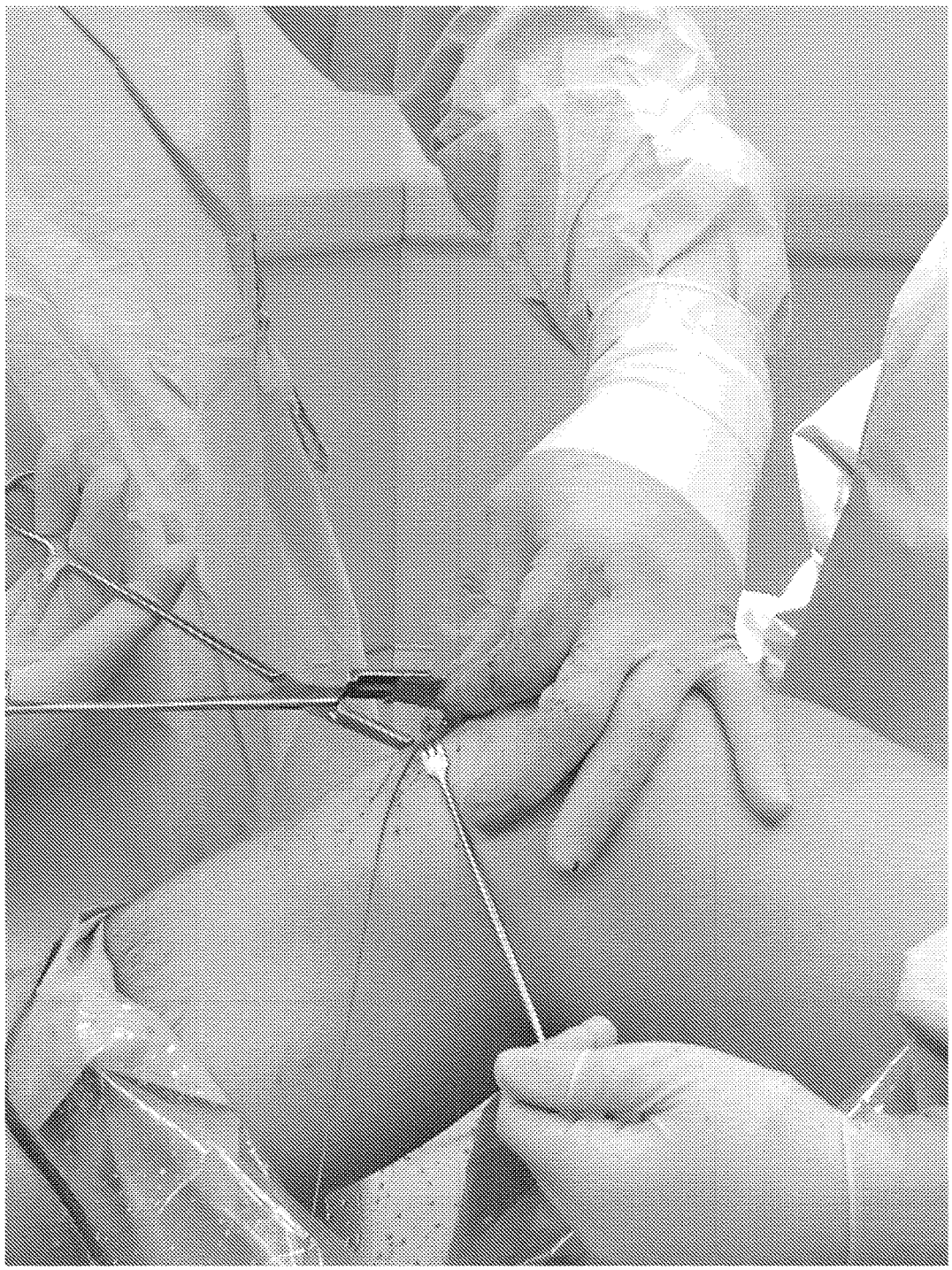
Figure 6:
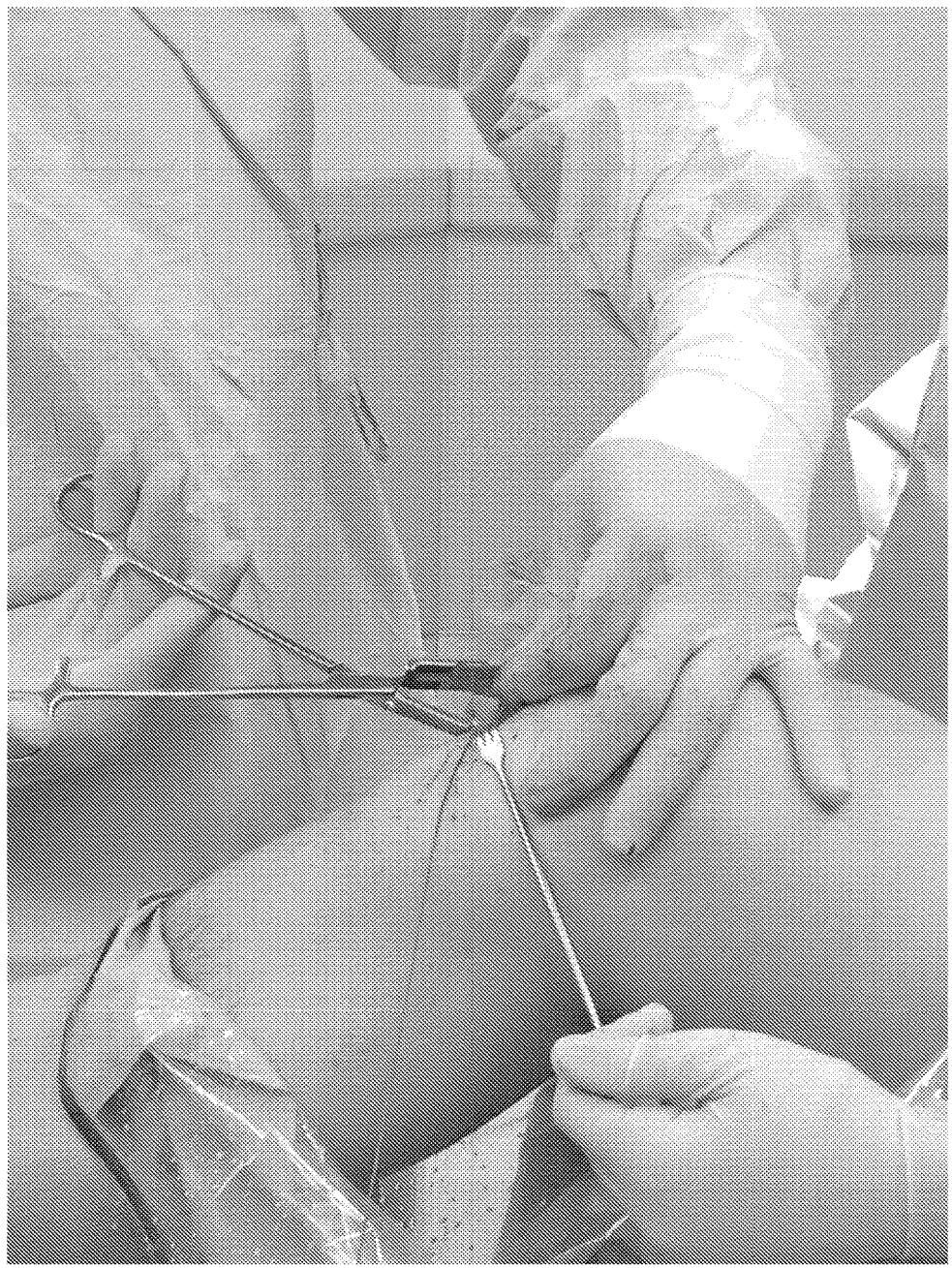
Figure 7:
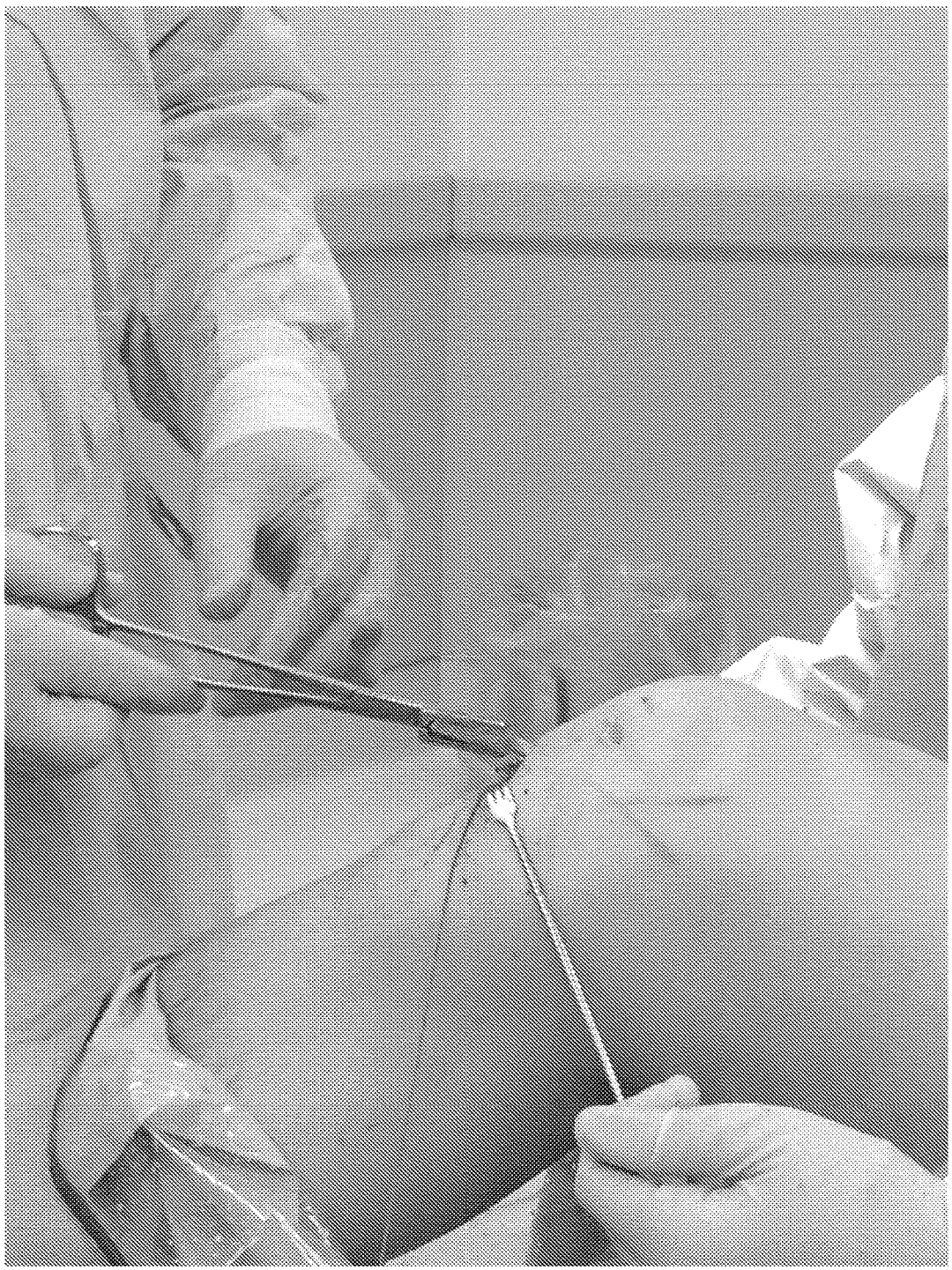
Figure 56:

The bone clamp 10 of the invention may be used in a variety of surgical procedures for trimming a bone tendon portion of a graft. One particular procedure in which the bone clamp 10 has been found to be particularly useful is for ACL repairs. FIGS. 4-56 illustrate such a procedure.

FIG. 4 shows the inferior pole of the patella tendon harvested from its insertion into the tibial tubercle.

FIGS. 5 through 11 show the bone clamp 10 of the invention grasping the bone tendon portion of the graft and securing it into place. Note that the clamp 10 is shaped like a trapezoid to cradle the bone graft which is harvested also in the shape of a trapezoid.

Figure 8:
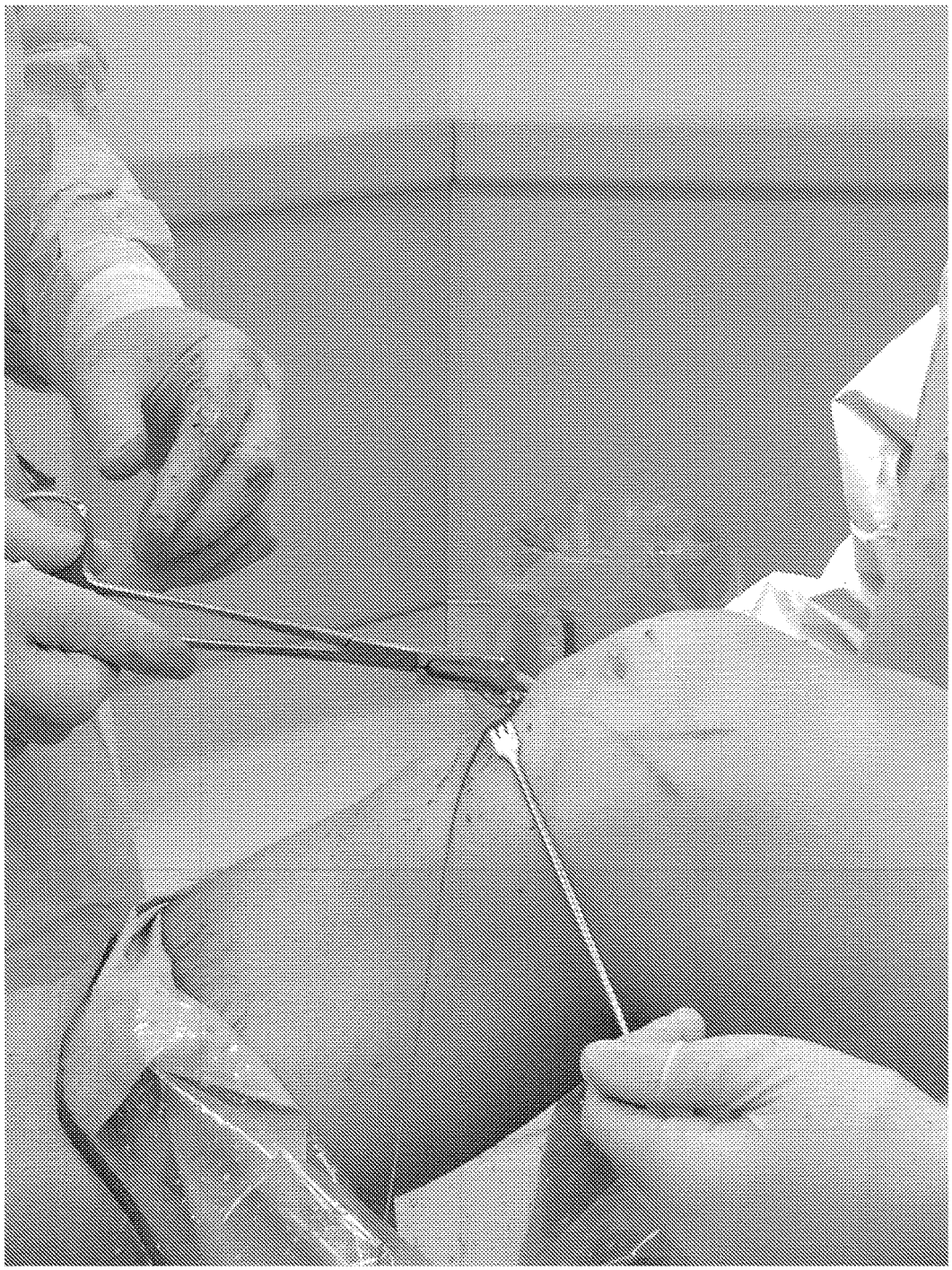
Figure 9:
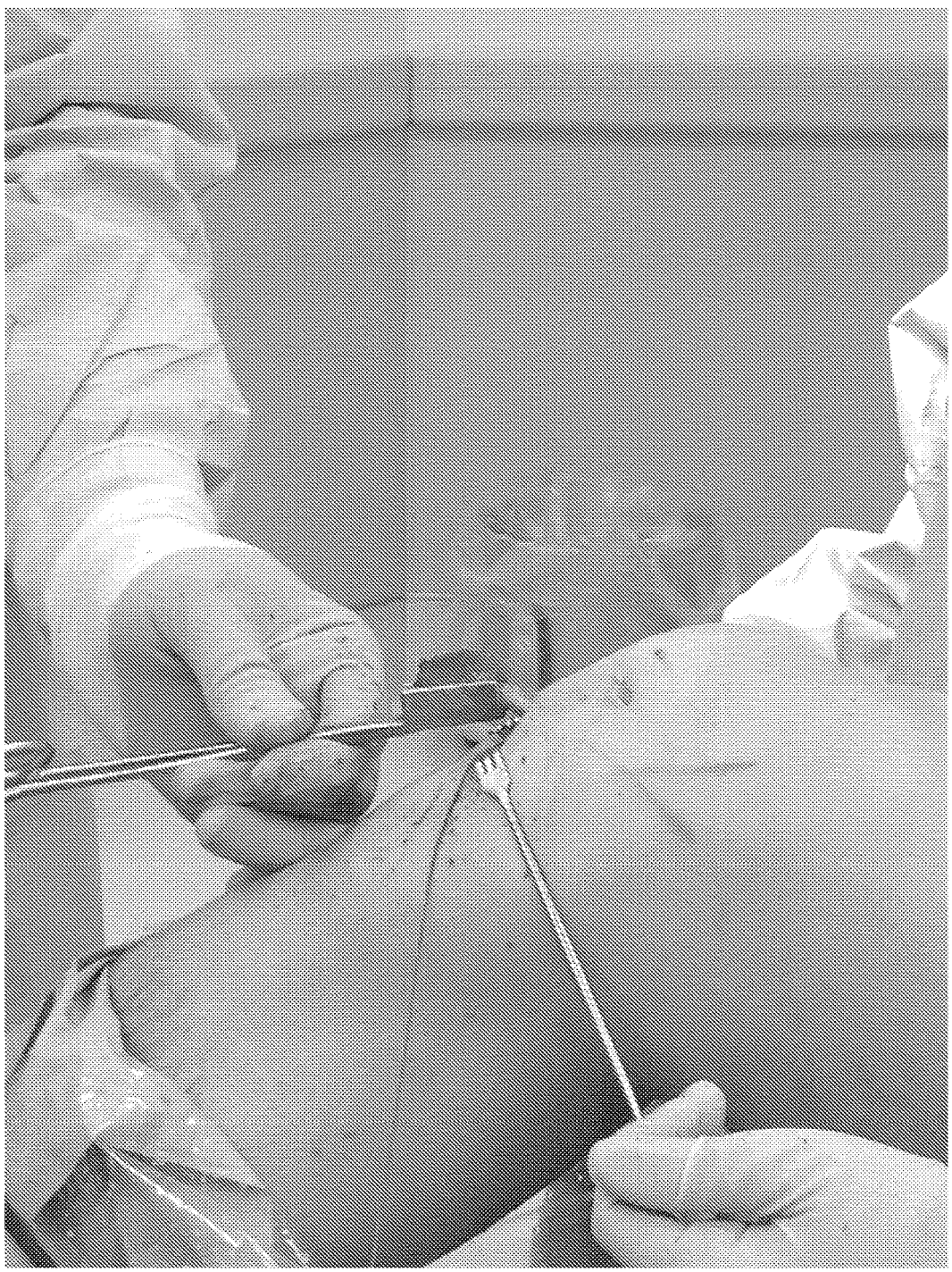
Figure 10:
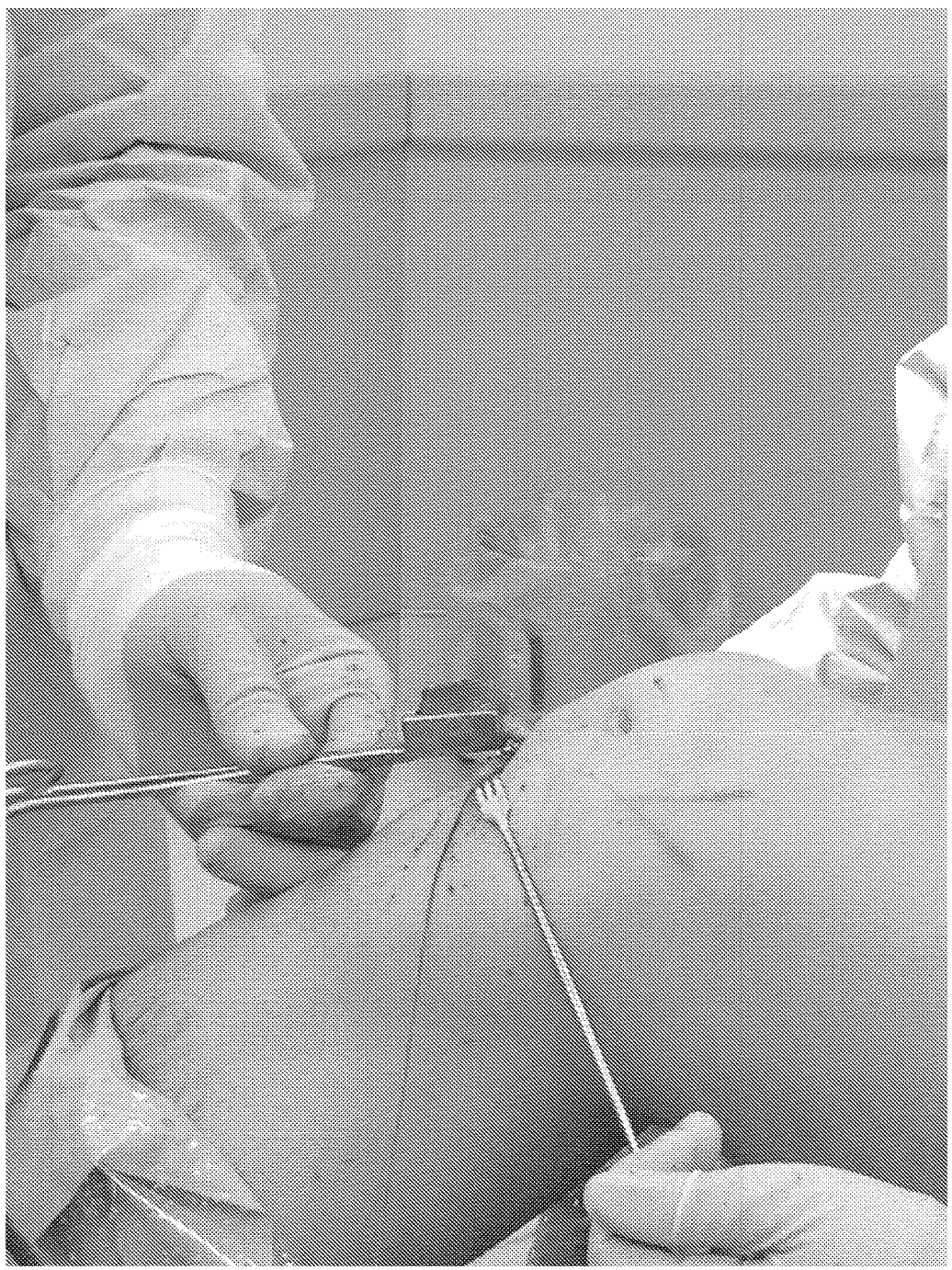
Figure 11:
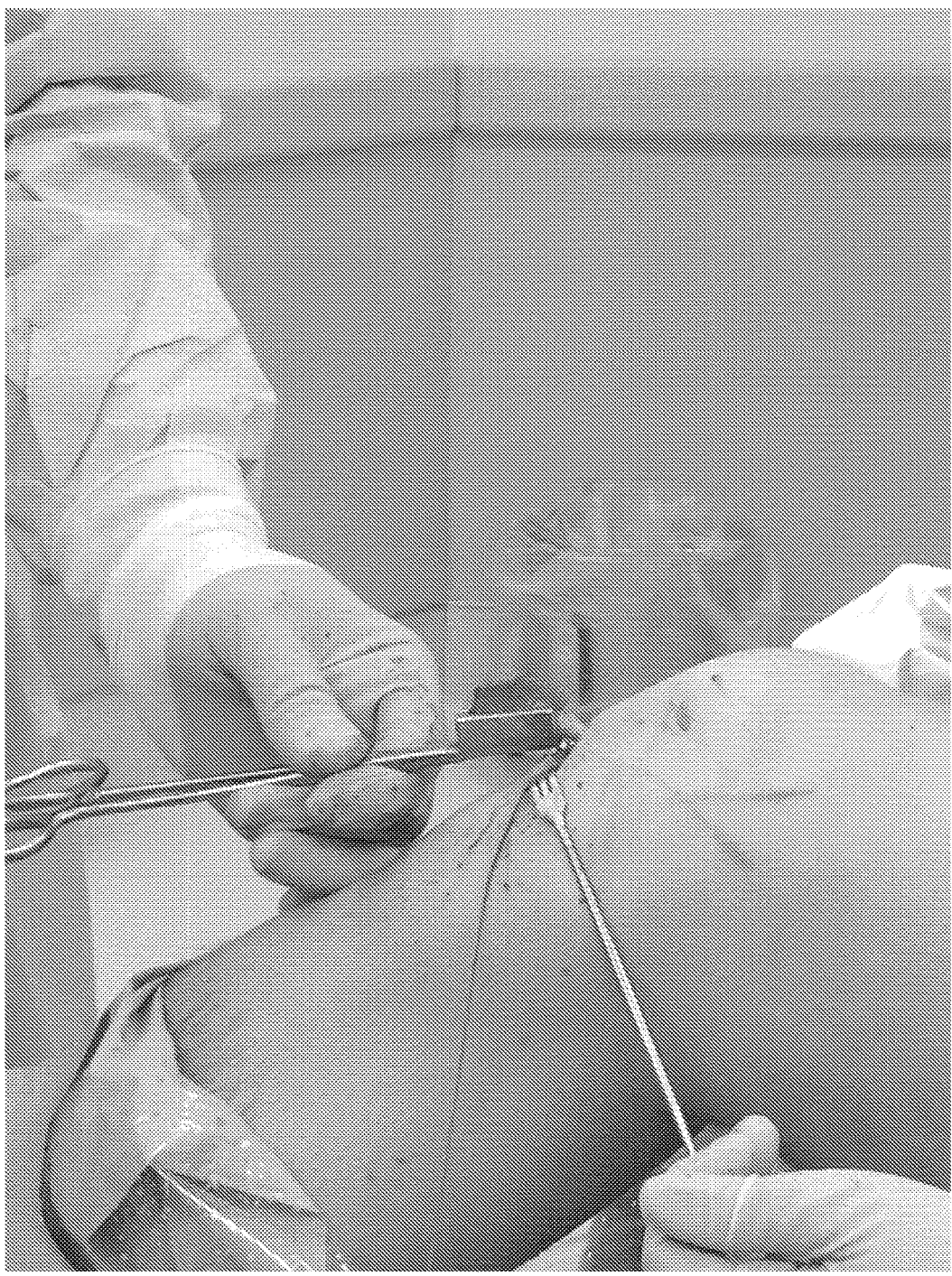

FIG. 8 shows the graft in the middle of the bone clamp secured into place. The clamp 10 provides a convenient cutting surface by virtue of the level, upper surfaces 28 and 30 of the upstanding walls 32 and 34. This cutting surface will support the saw blade as it makes a smooth straight cut along the top portion of the bone plug. It is the measured (e.g., 10 mm) cutting surface of the upper surfaces 28 and 30 for the bone plug and the security of the graft in the clamp that provides the new advantage of using this clamp 10 in surgery.

Figure 12:
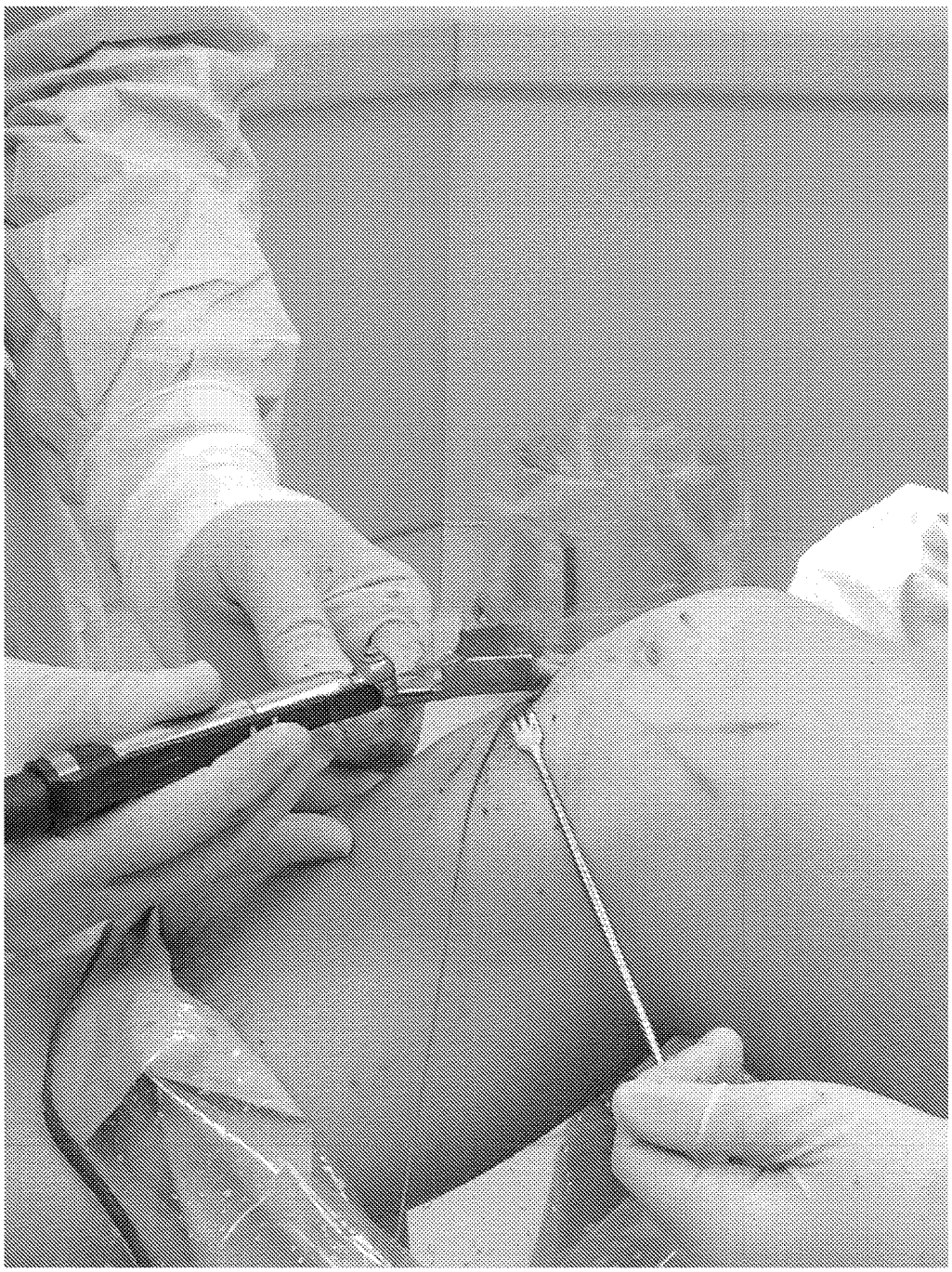
Figure 13:
Figure 14:
Figure 15:
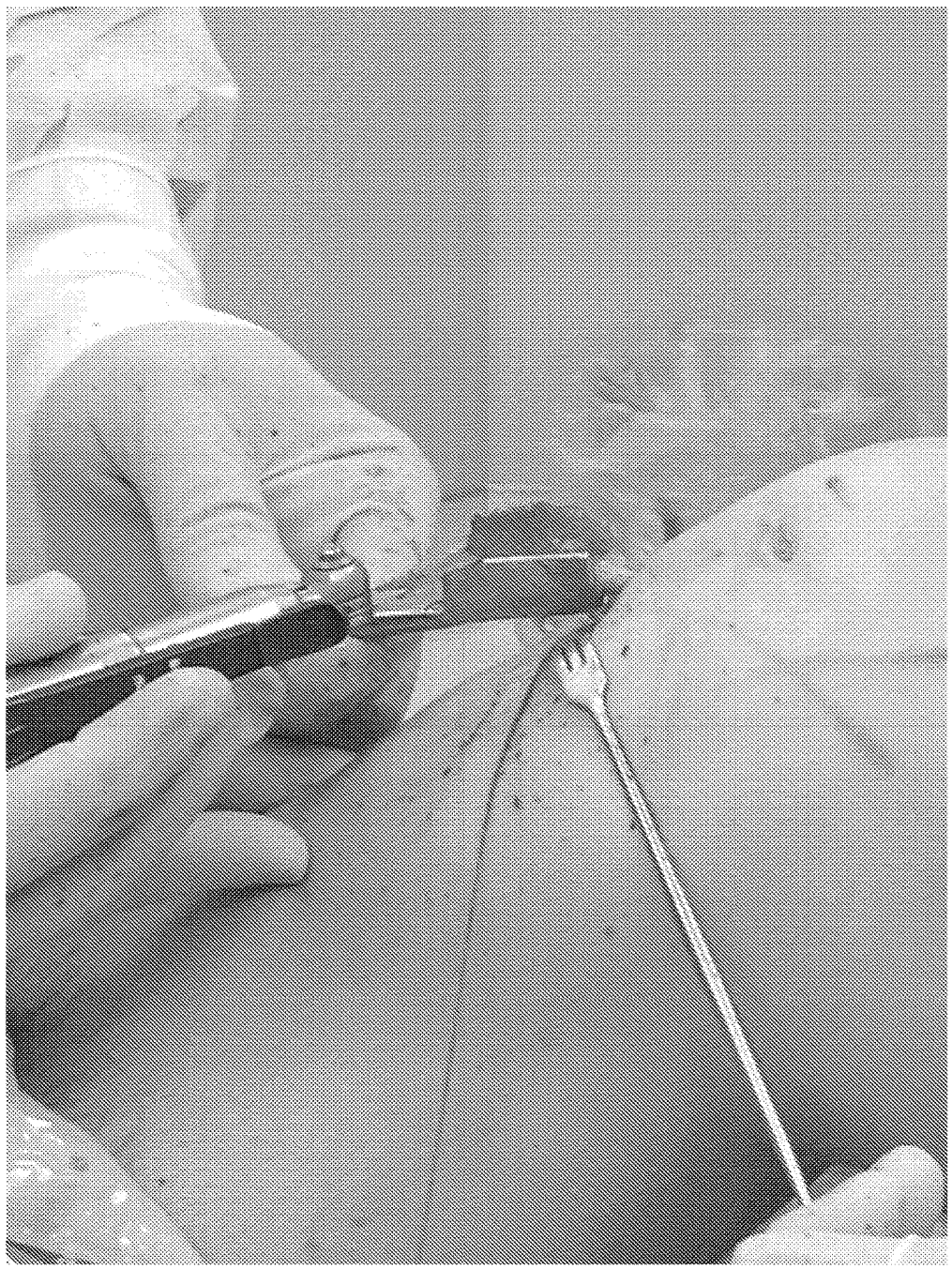
Figure 16:
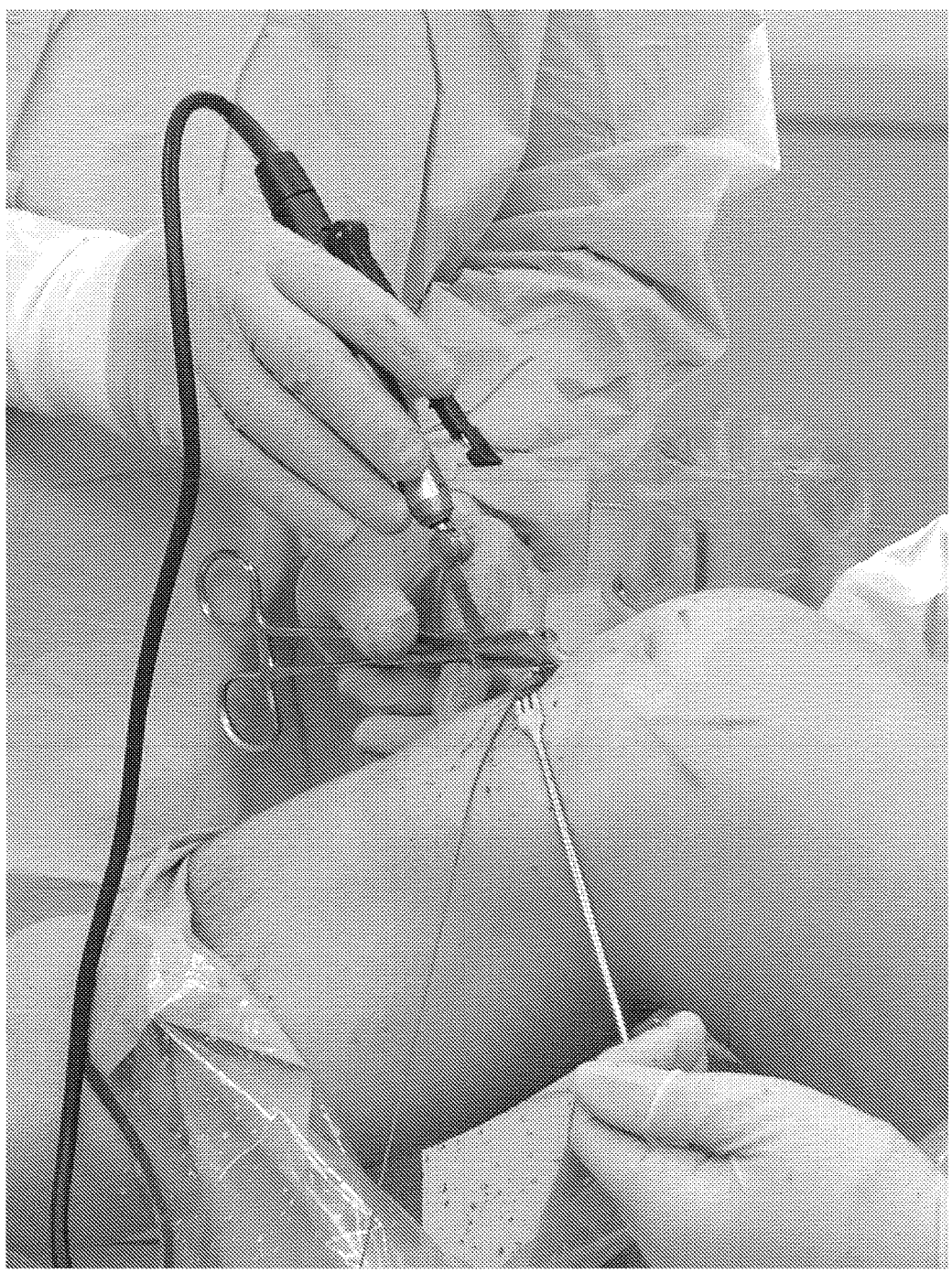
Figure 17:
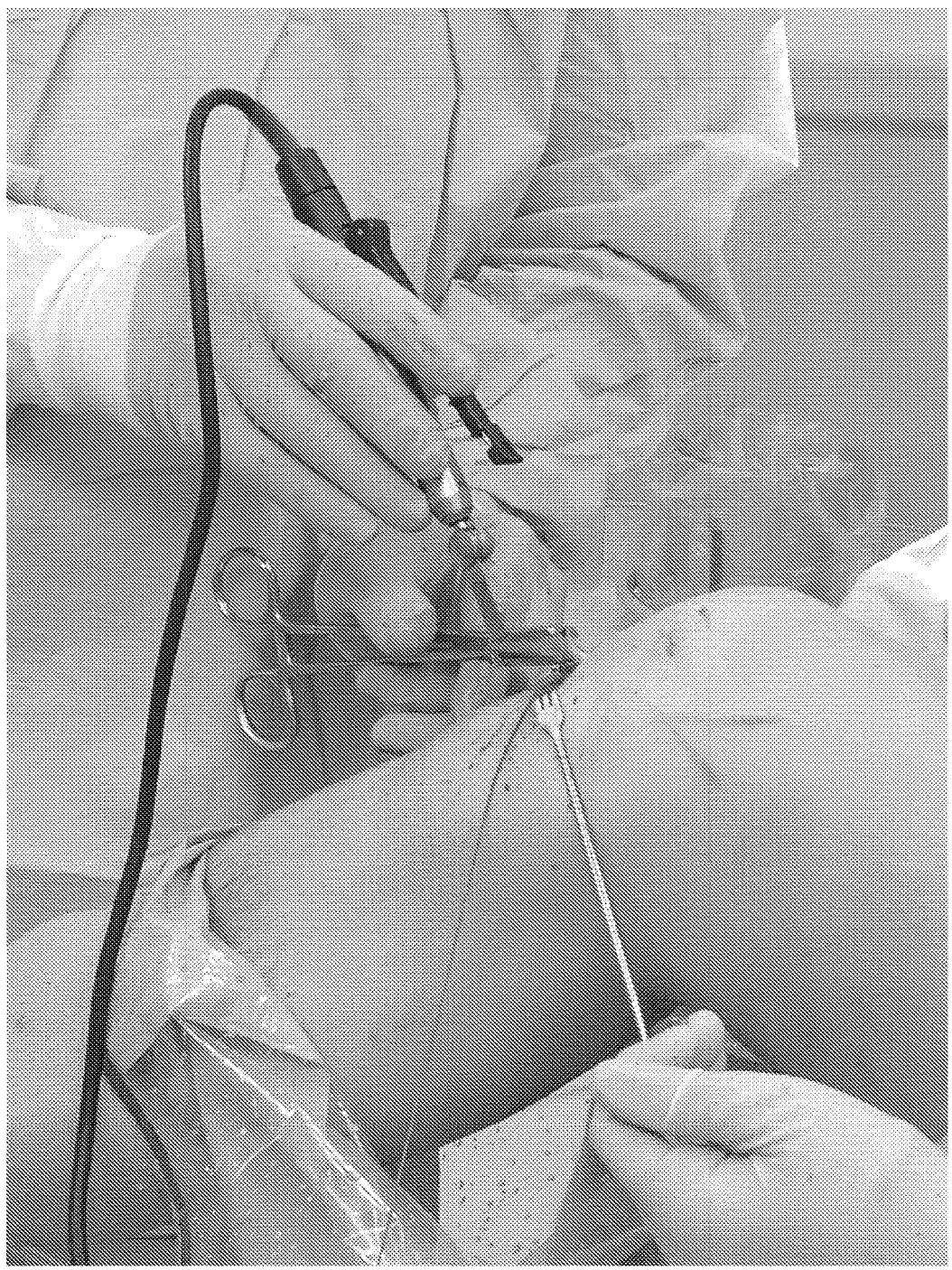
Figure 18:
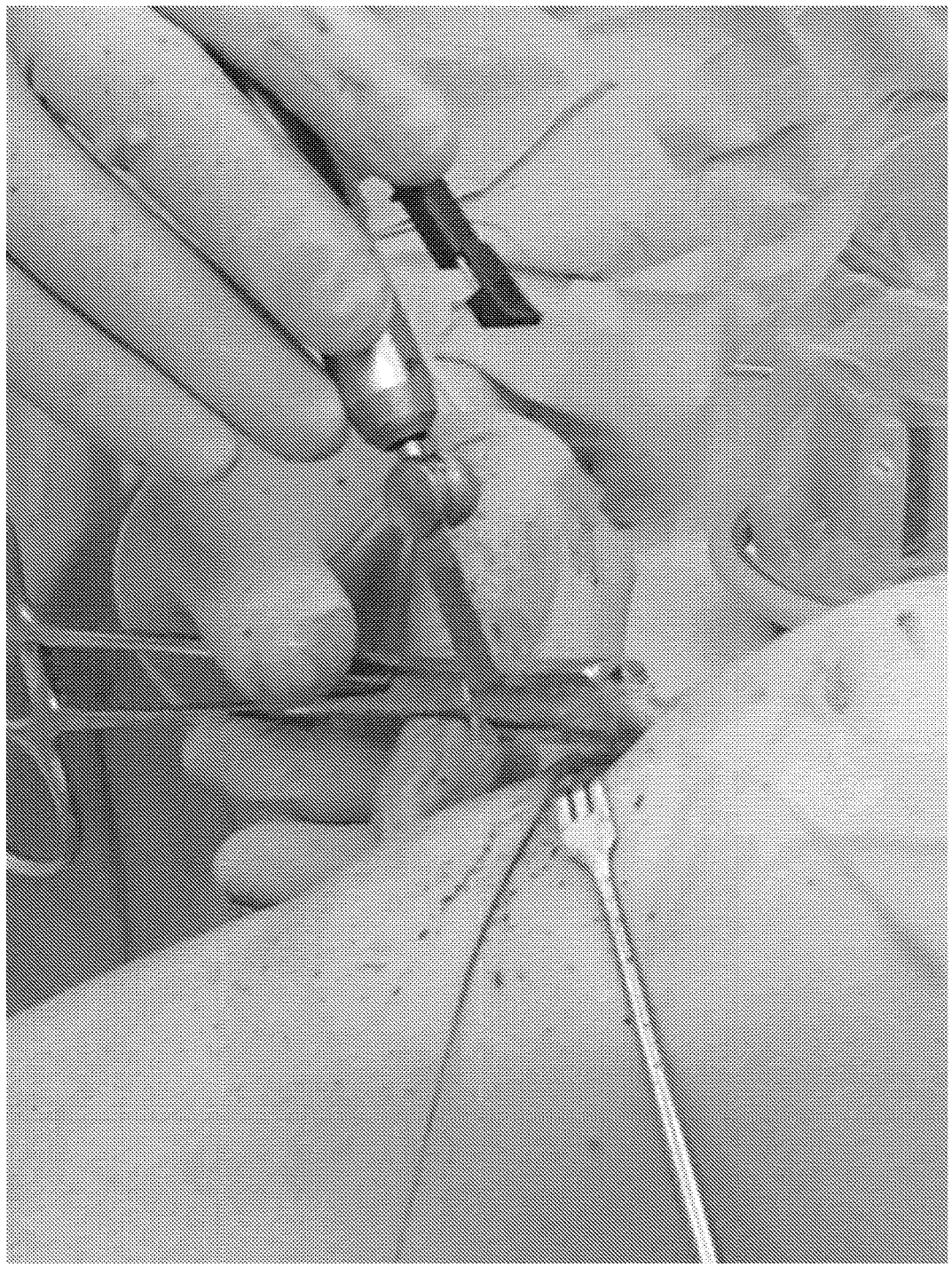
Figure 19:
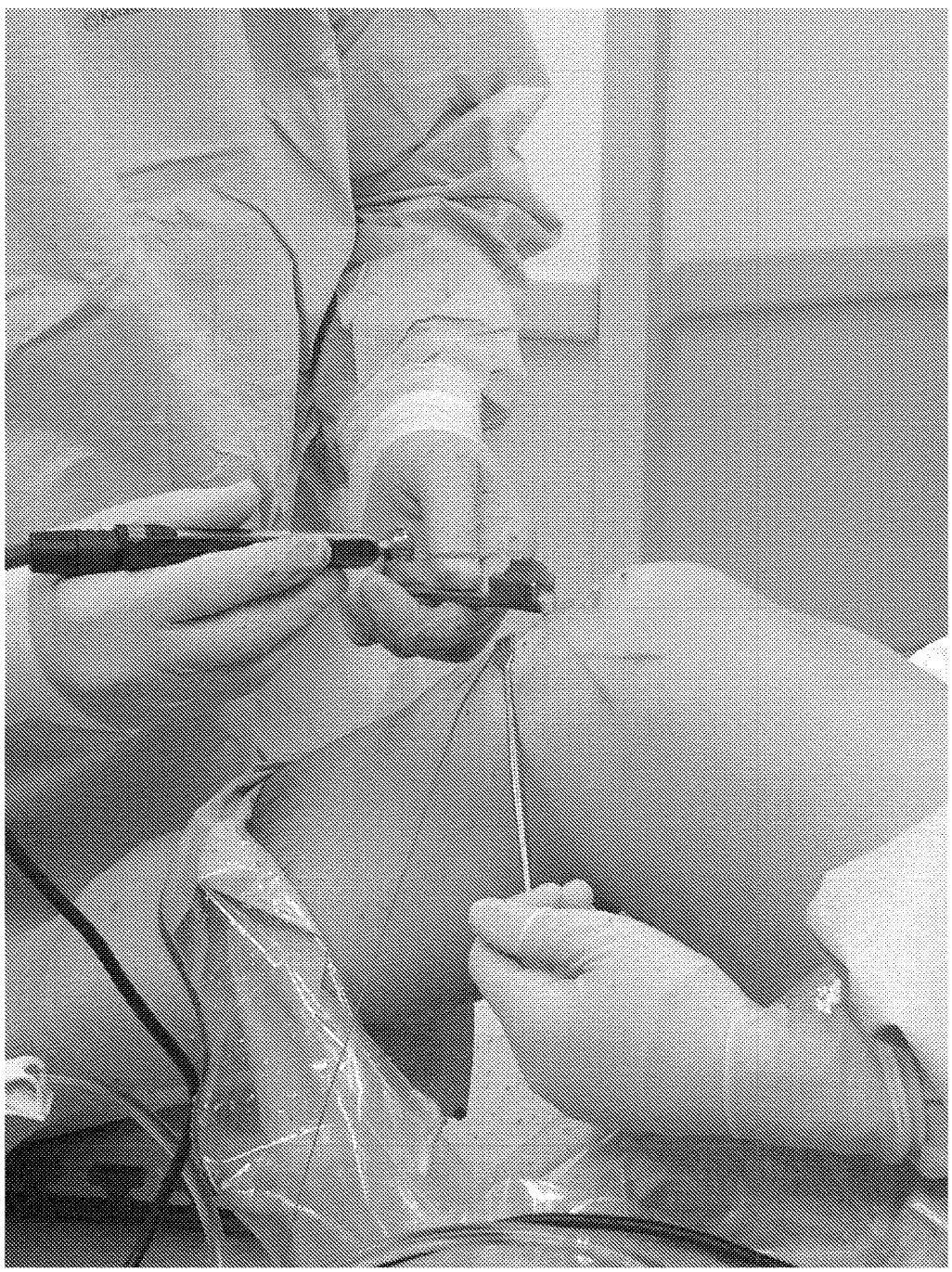
Figure 20:
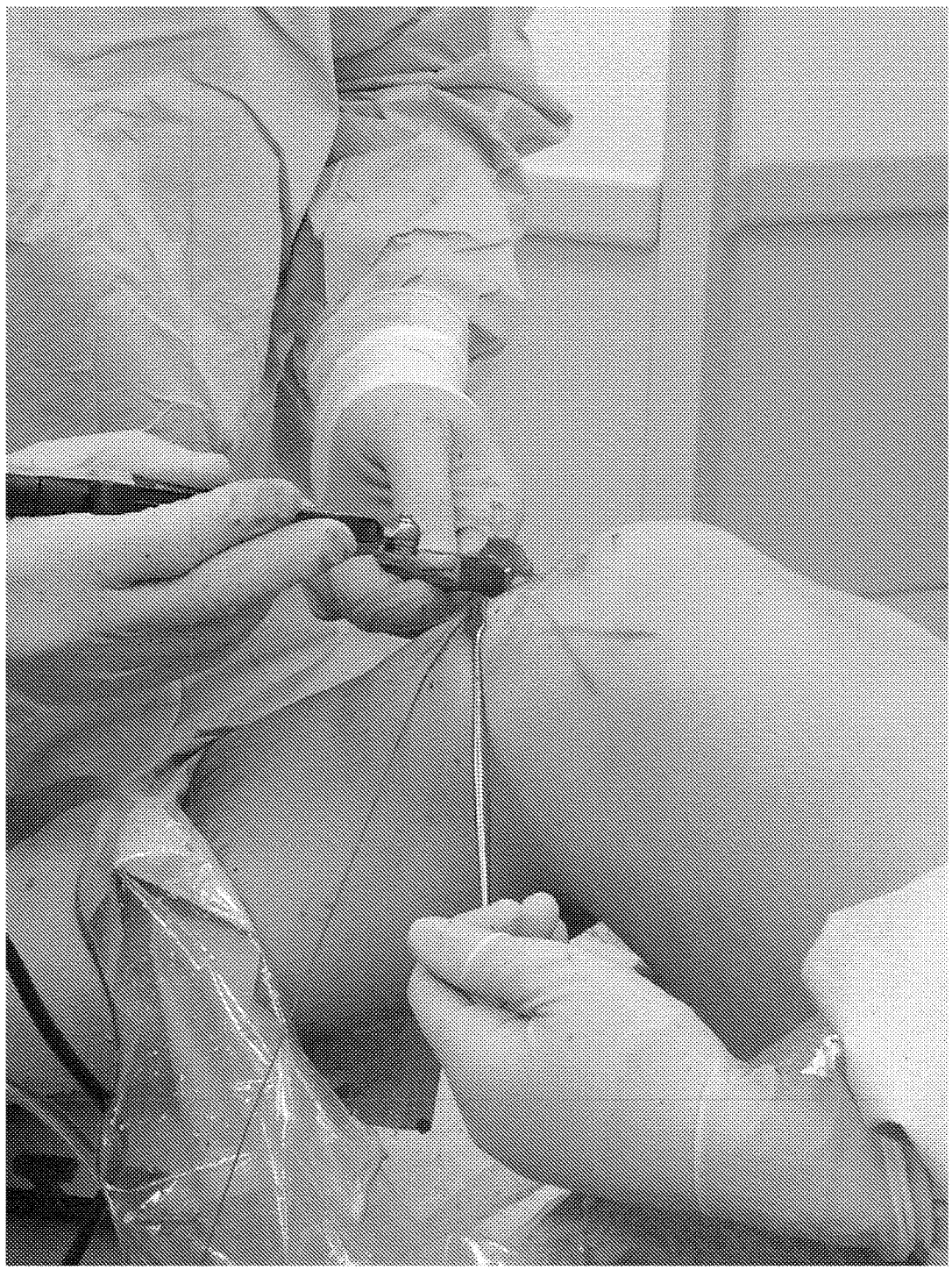
Figure 21:
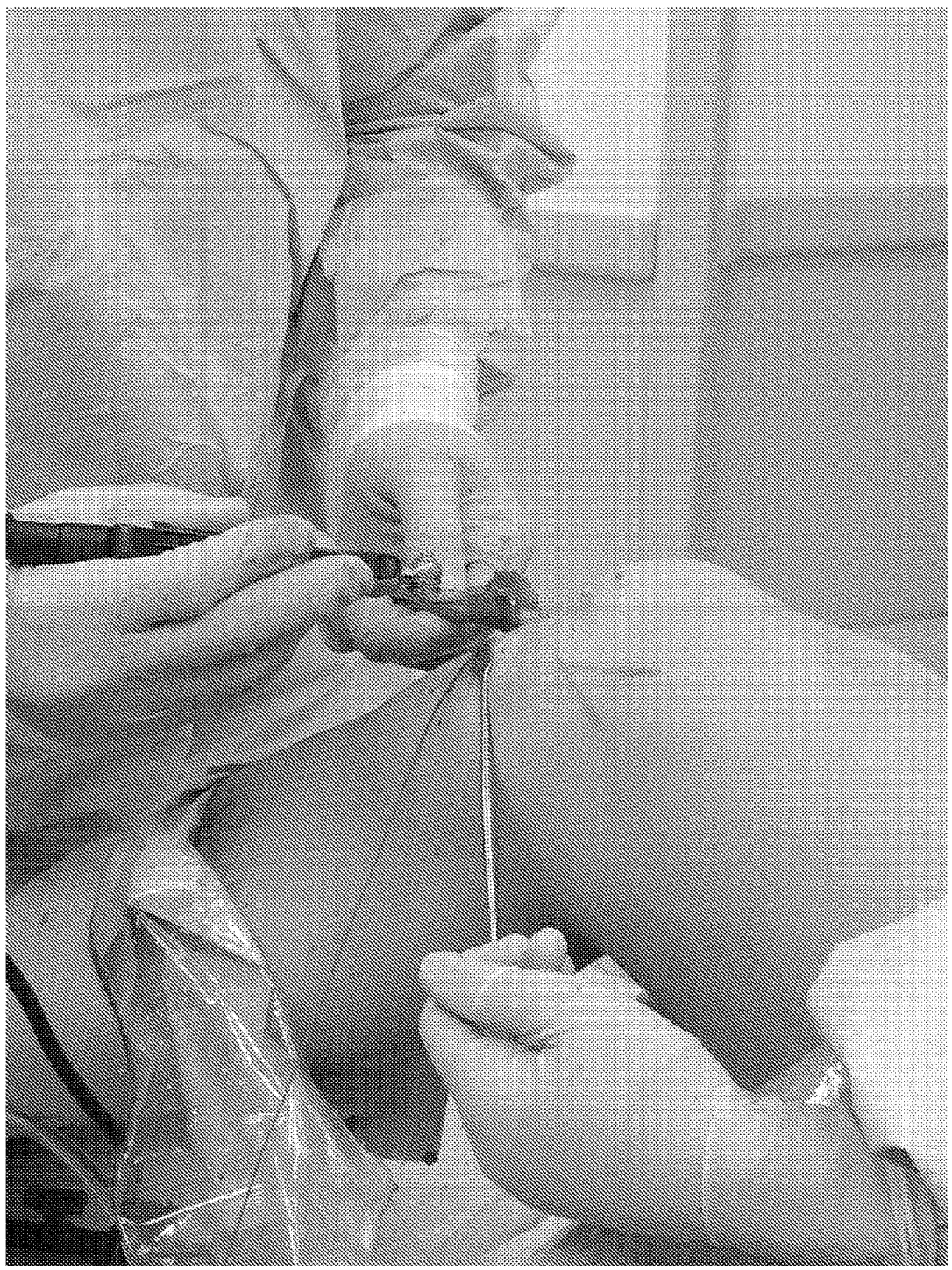
Figure 22:
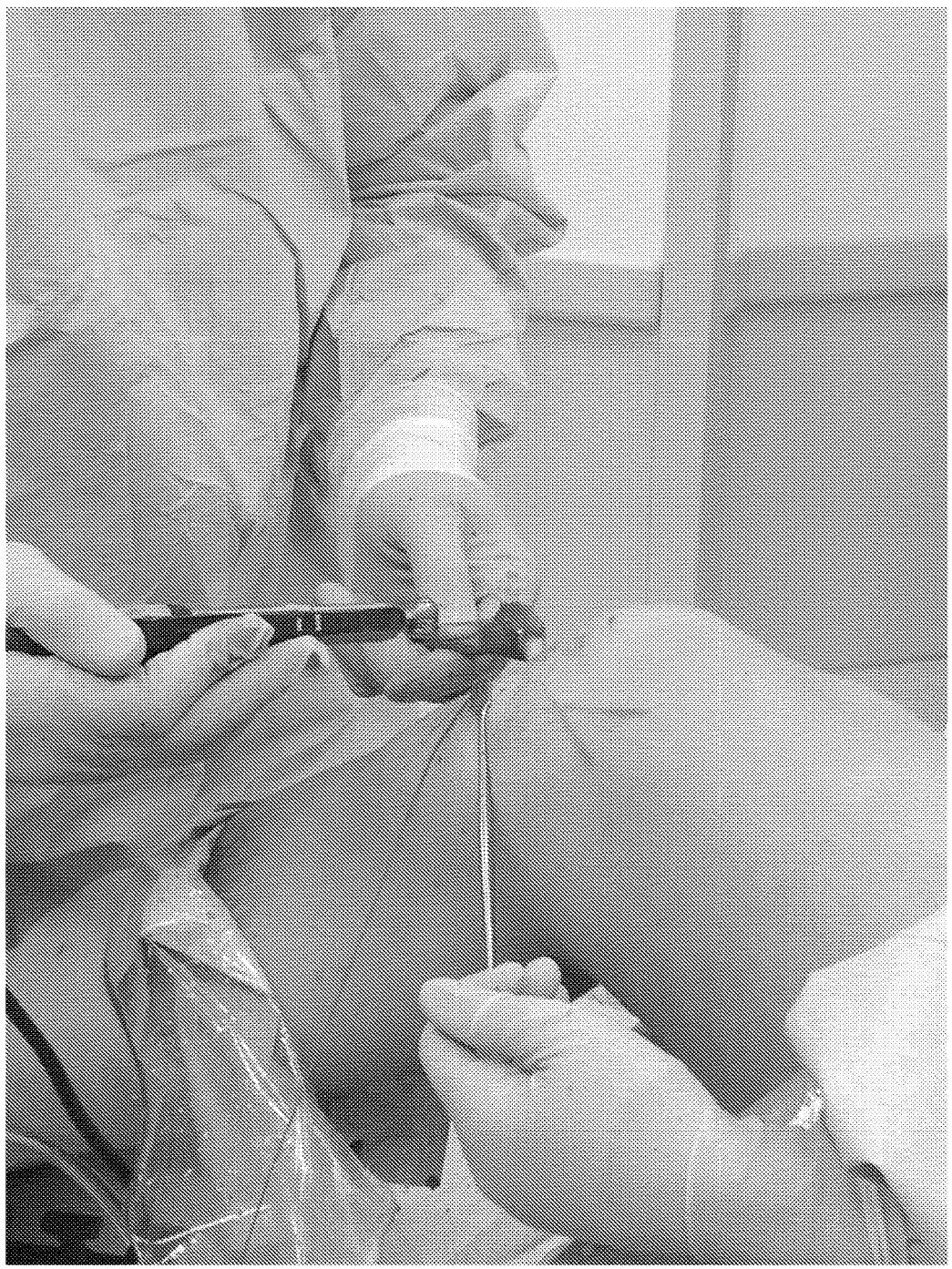
Figure 23:
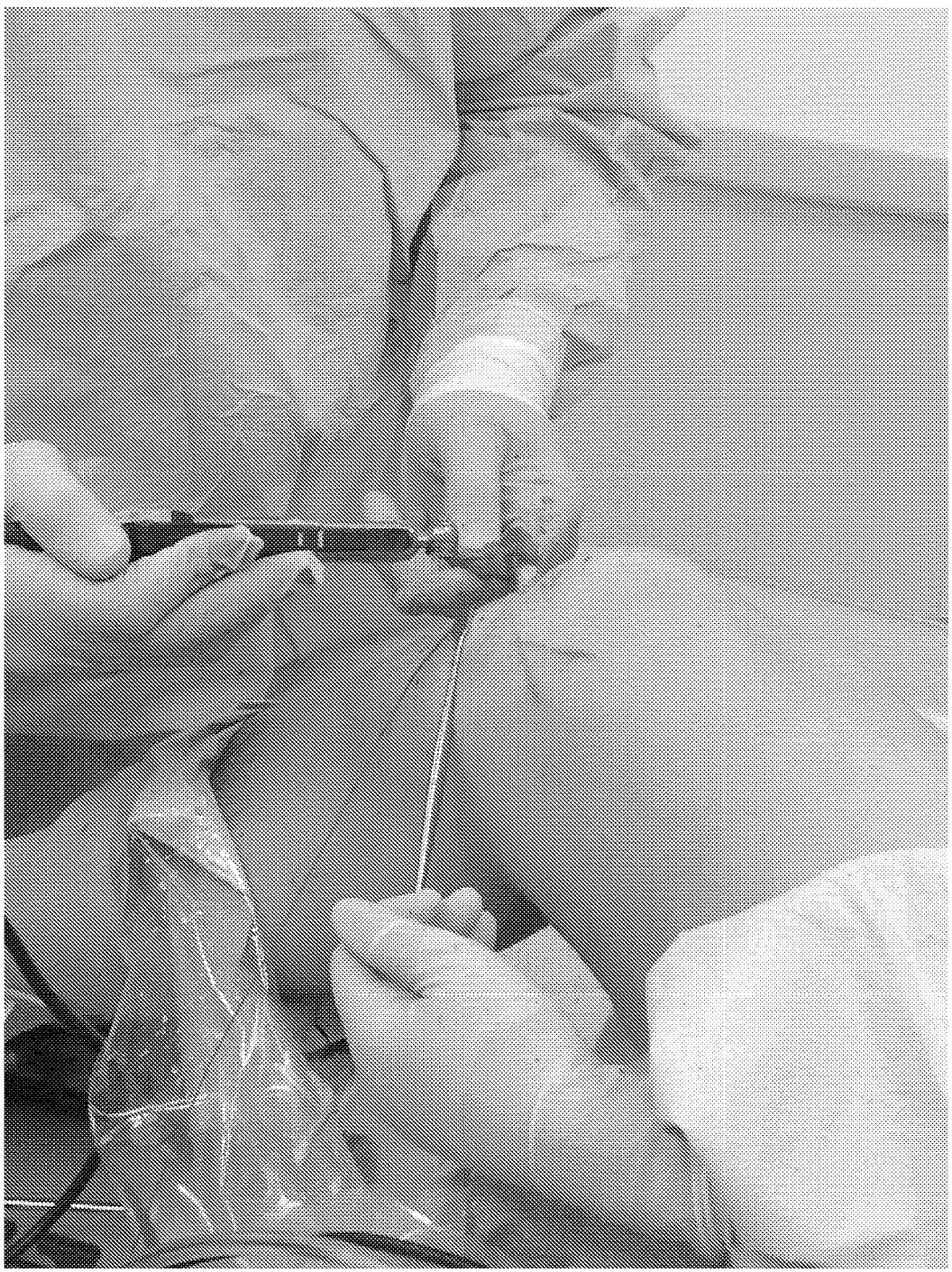
Figure 24:
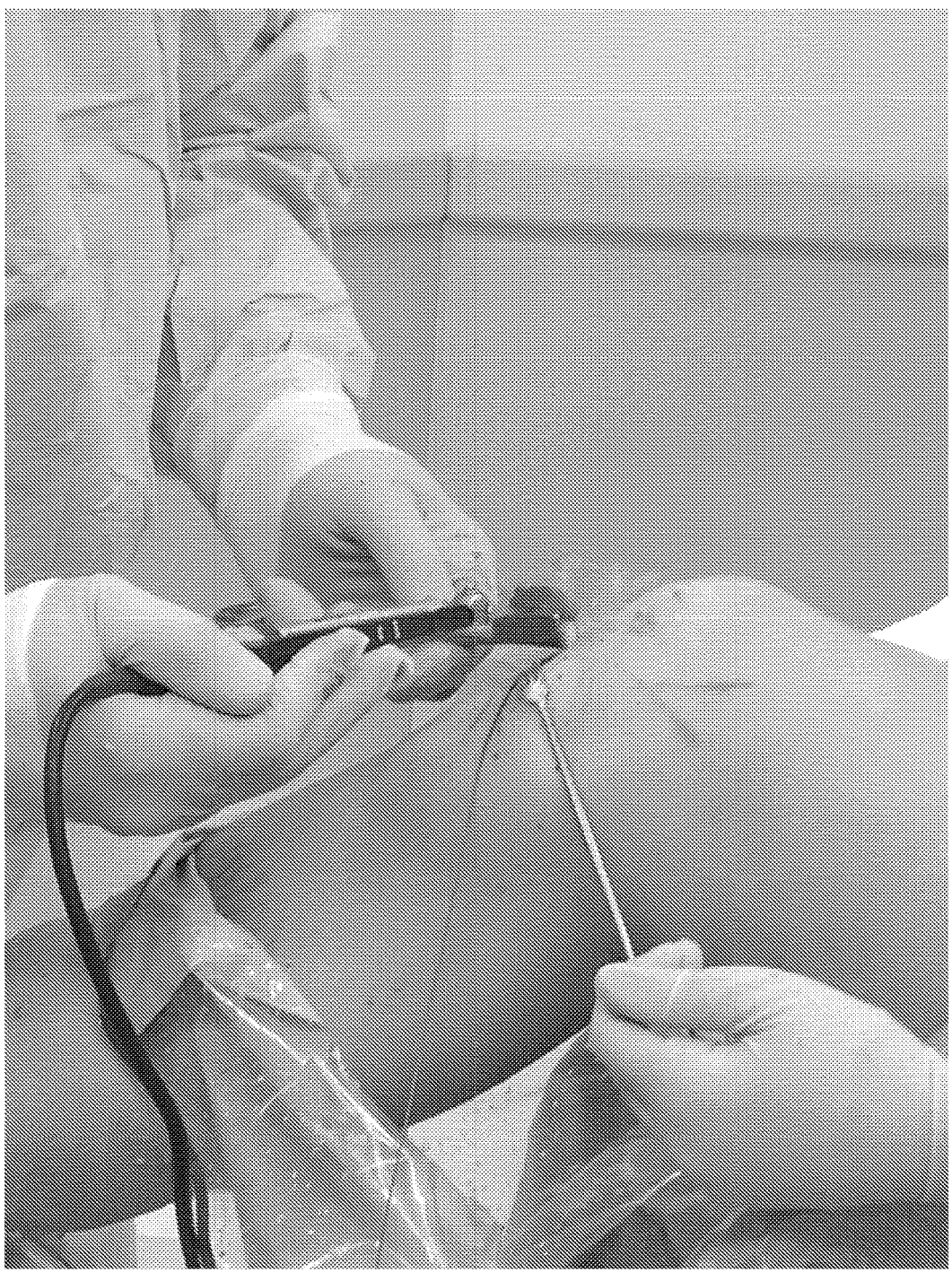
Figure 25:
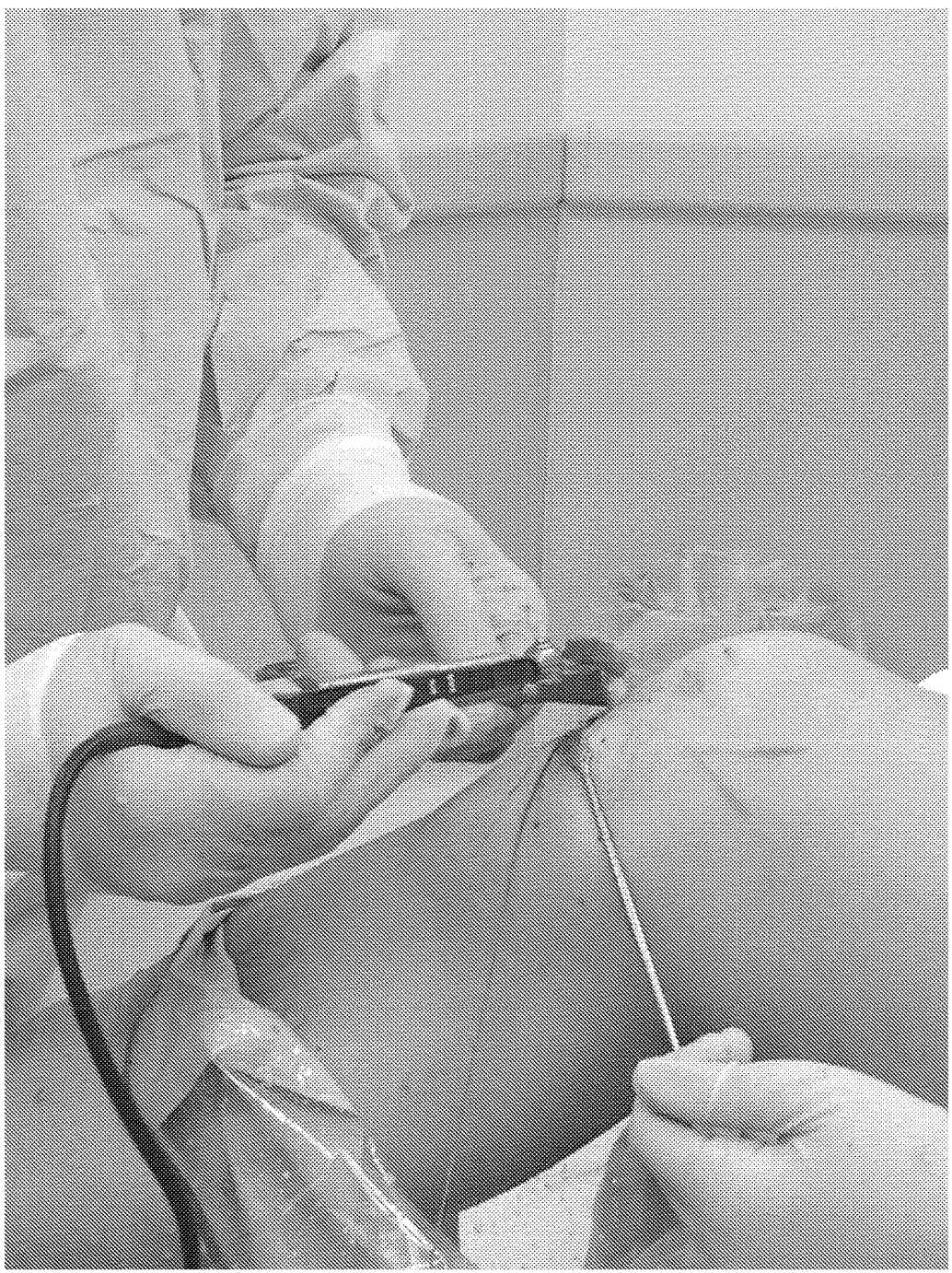

FIG. 12 shows the saw blade being used against the upper surfaces 28 and 30 of the clamp 10 to cut a precise (e.g., 10 mm) bone plug that is attached to the patella tendon. This provides a uniform graft fit within the bone tunnel that leads to the reconstruction of the ACL.

FIGS. 12 through 25 show the saw blade being used against the upper surfaces 28 and 30 of the clamp 10 to obtain a very precise bone plug.

Figure 26:
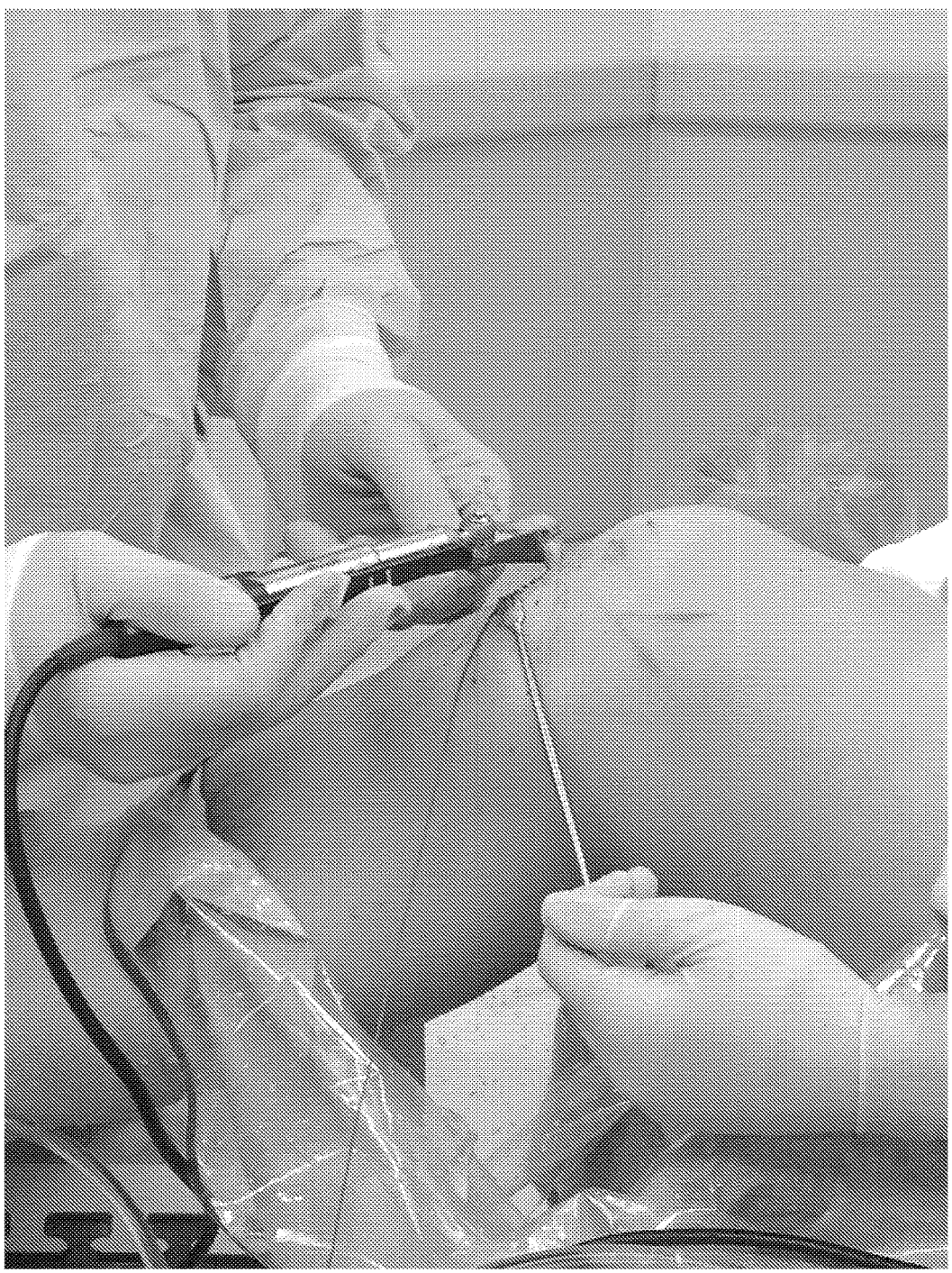
Figure 27:
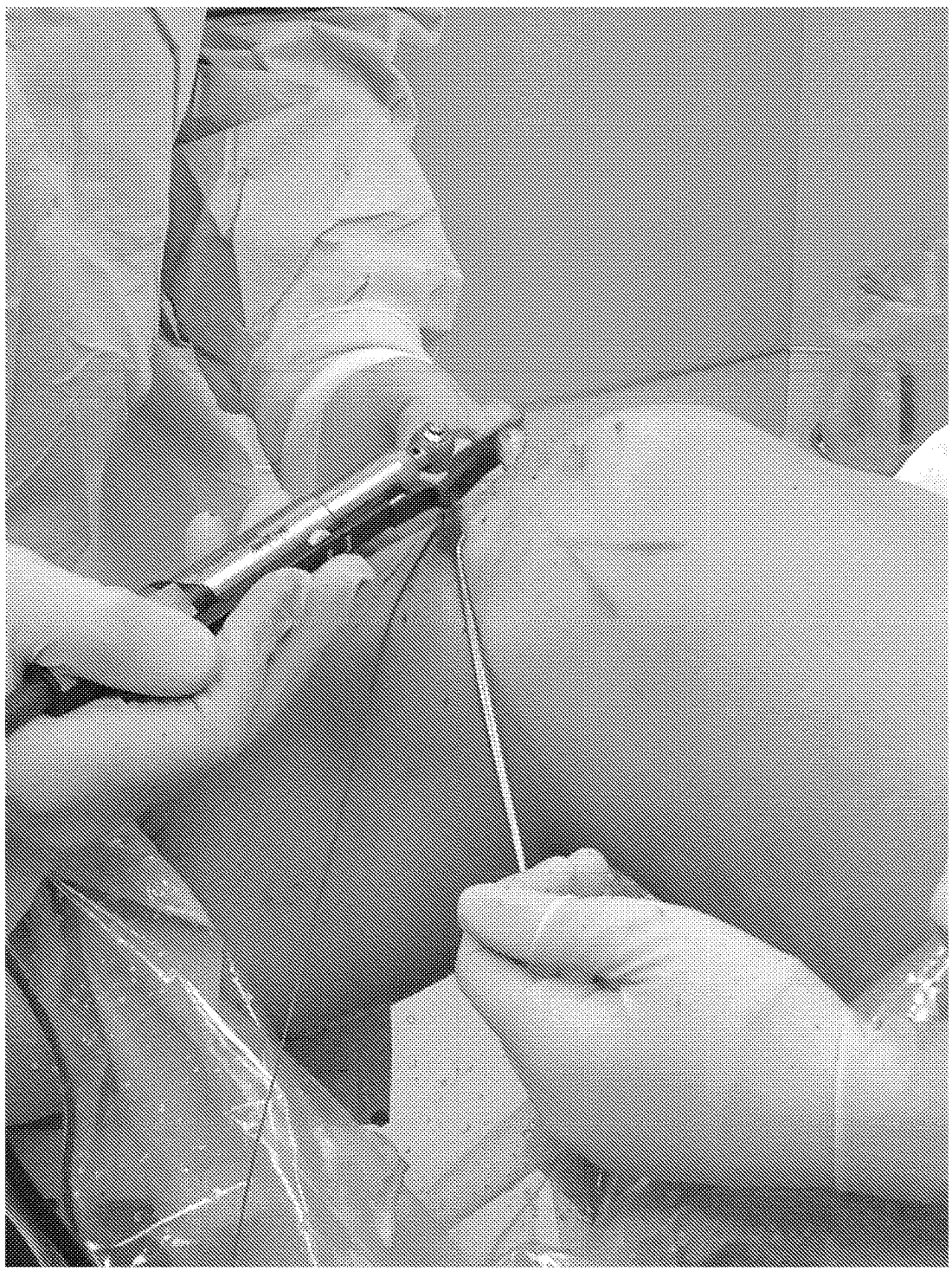
Figure 28:
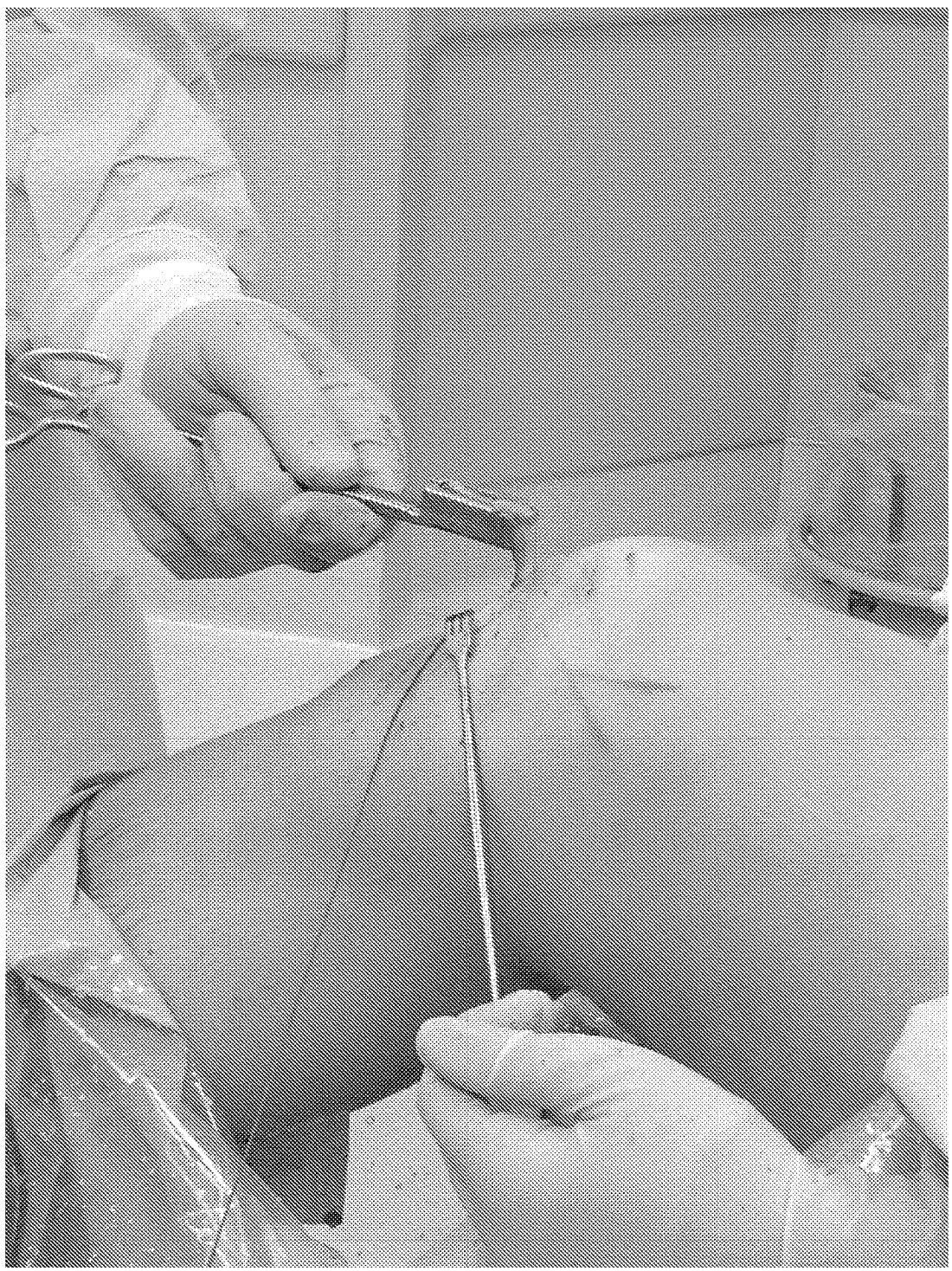
Figure 29:
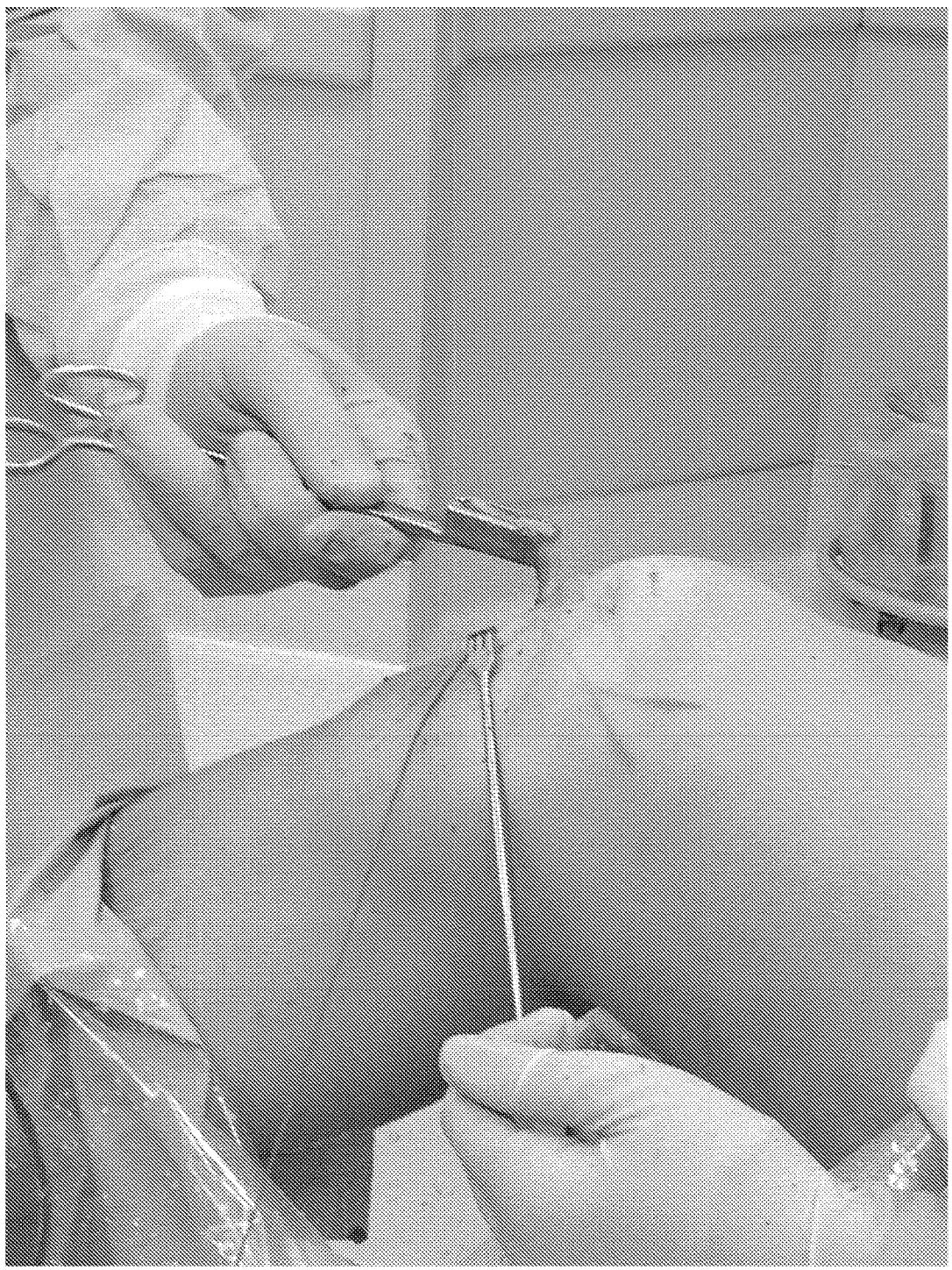
Figure 30:
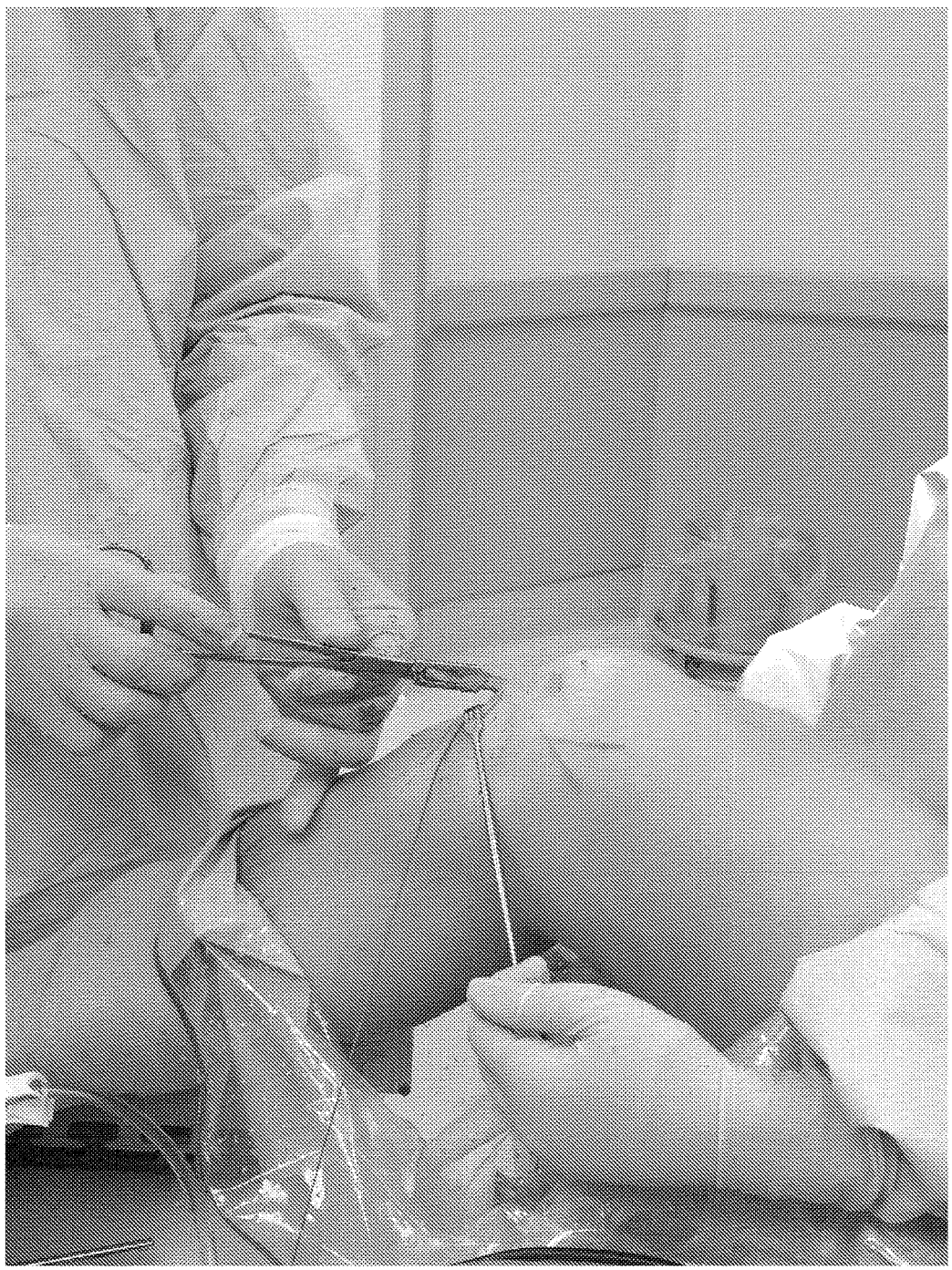
Figure 31:
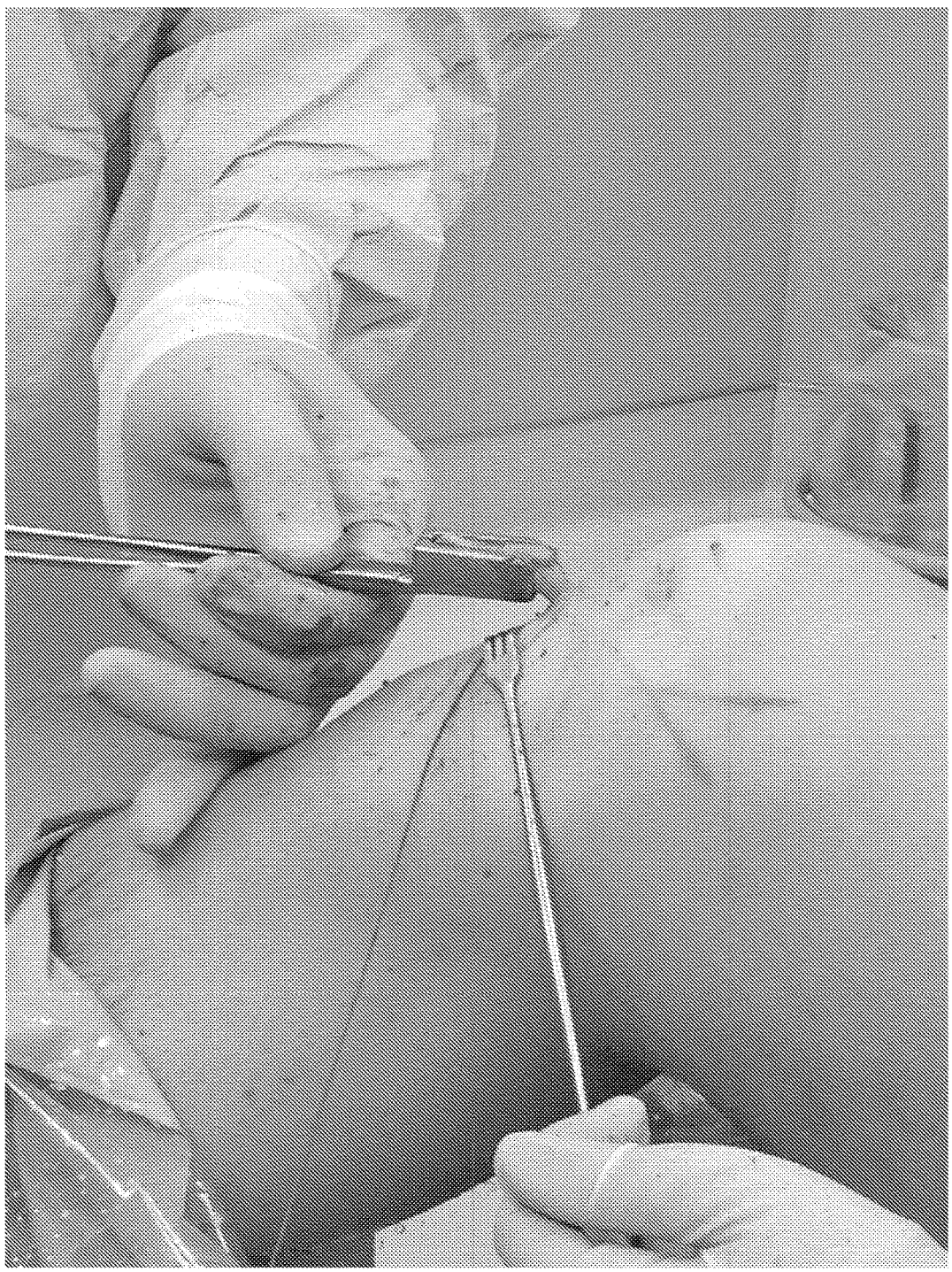
Figure 32:
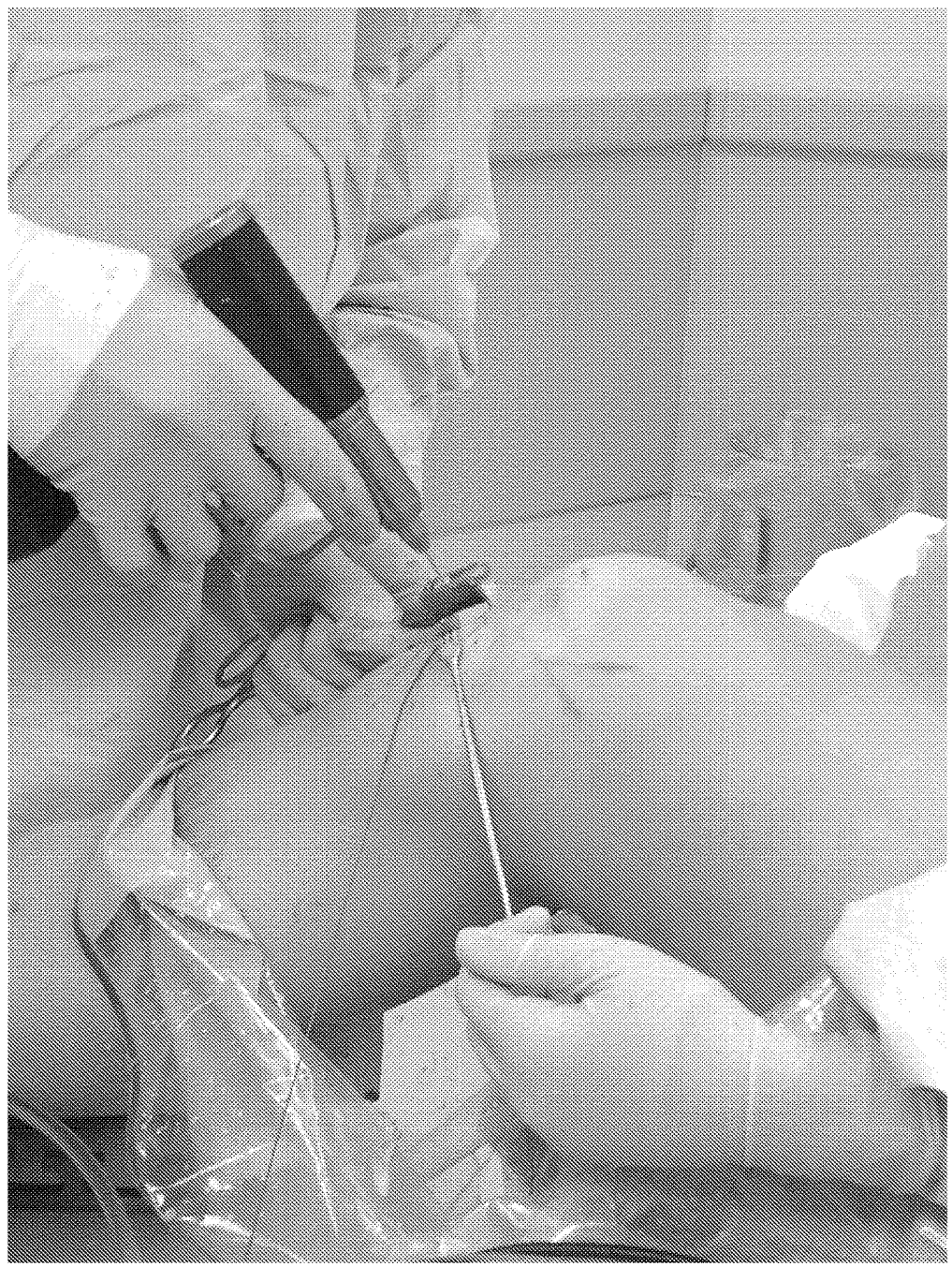
Figure 33:
Figure 34:
Figure 35:
Figure 36:
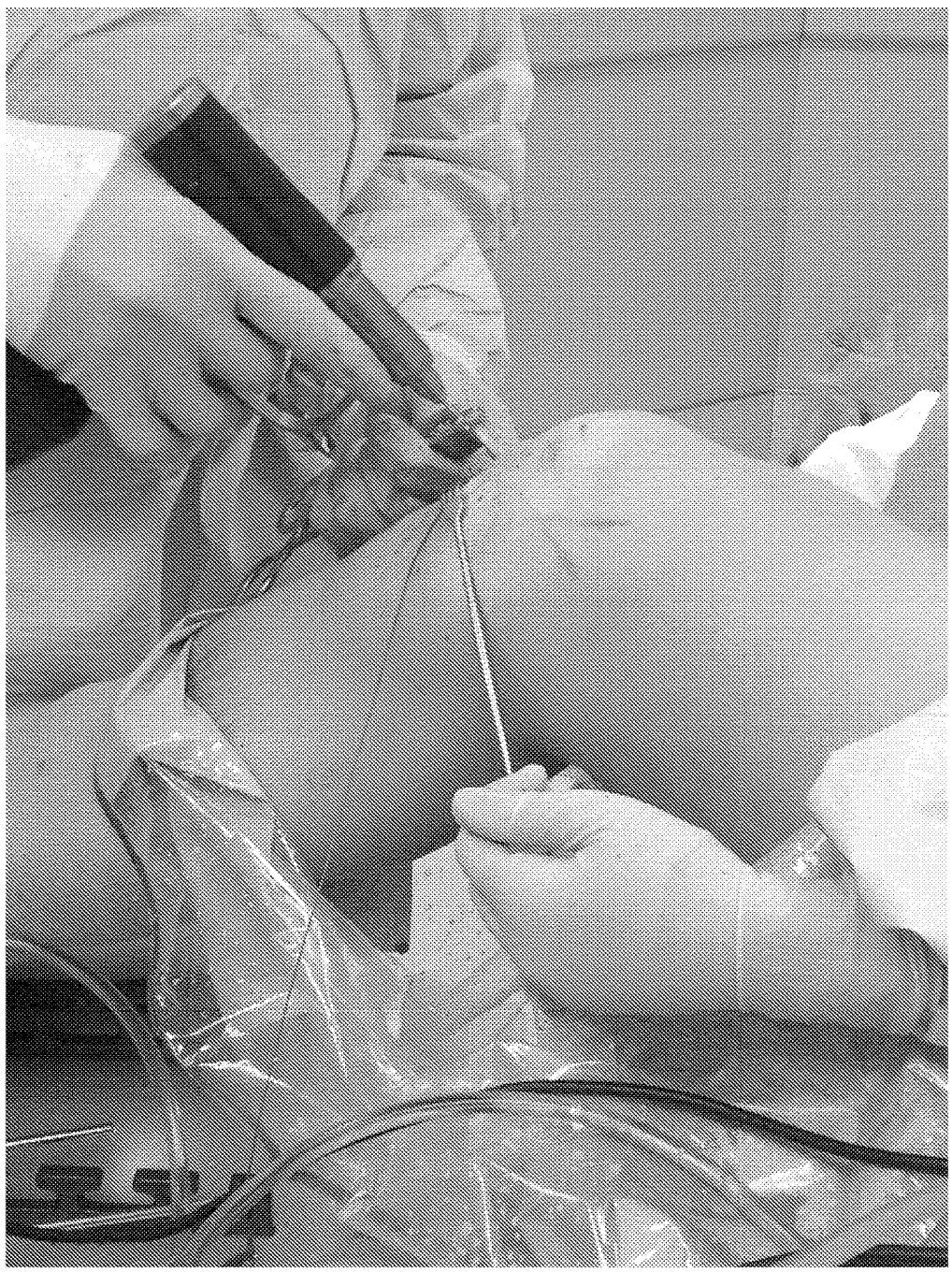

FIGS. 26 and 27 show a second pass of the saw blade over the bone plug to make sure that there are no rough edges that may possibly get caught up in the boney hole/tunnel.

FIGS. 28 through 31 show the bone plug after it is contoured in the grasp of the clamp 10.

FIGS. 32 through 36 show the bone plug being drilled with a drill bit to make holes to receive the large number five tycron sutures.

Figure 37:
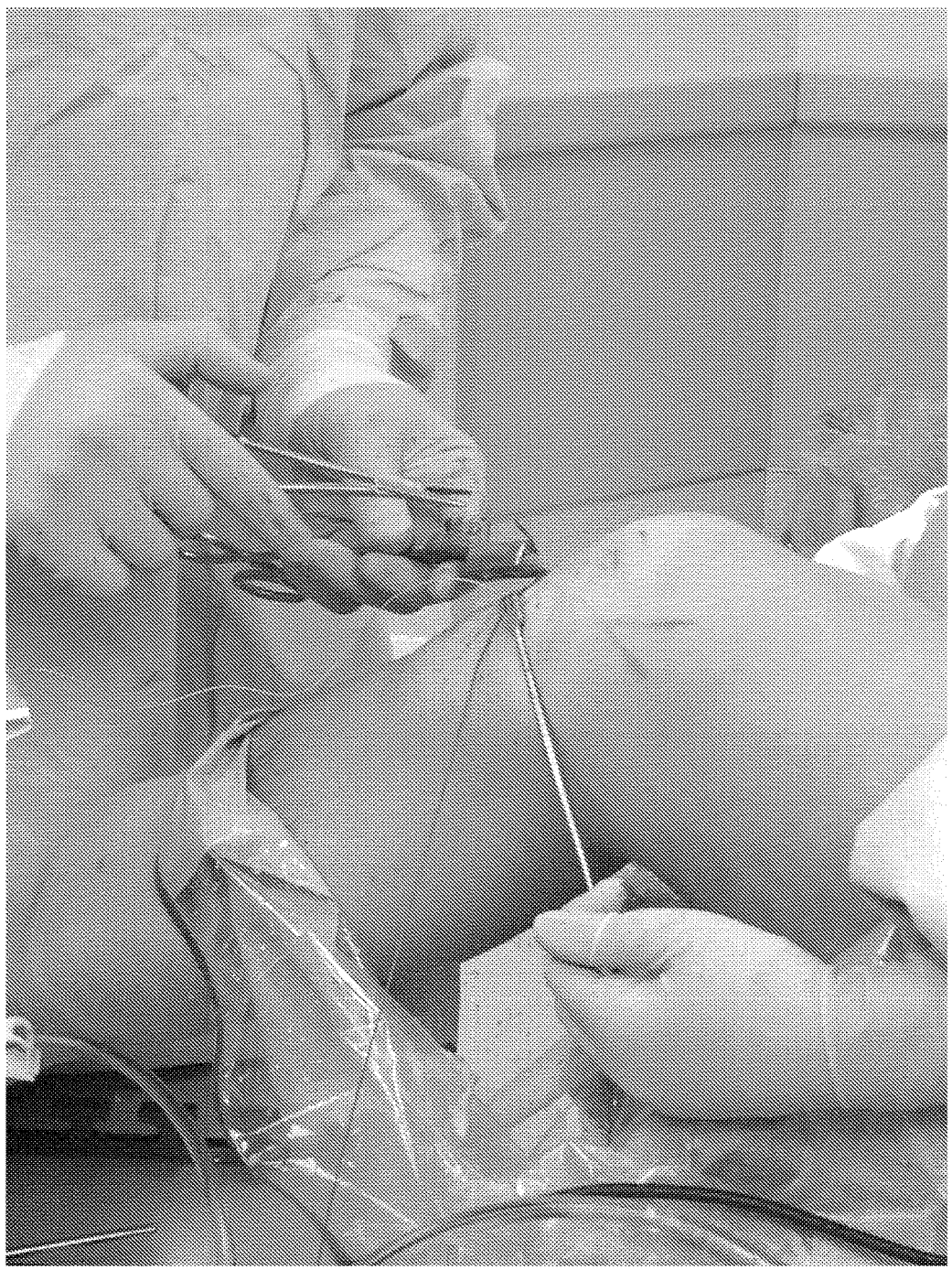

FIG. 37 shows the sutures are being placed through the graft so that the graft can be secured into the knee joint. The graft on the patella side is secured with a button. The graft on the tibial side is secured with a screw and washer. The sutures loop around the screw and washer to help hold the graft in place.

Figure 38:
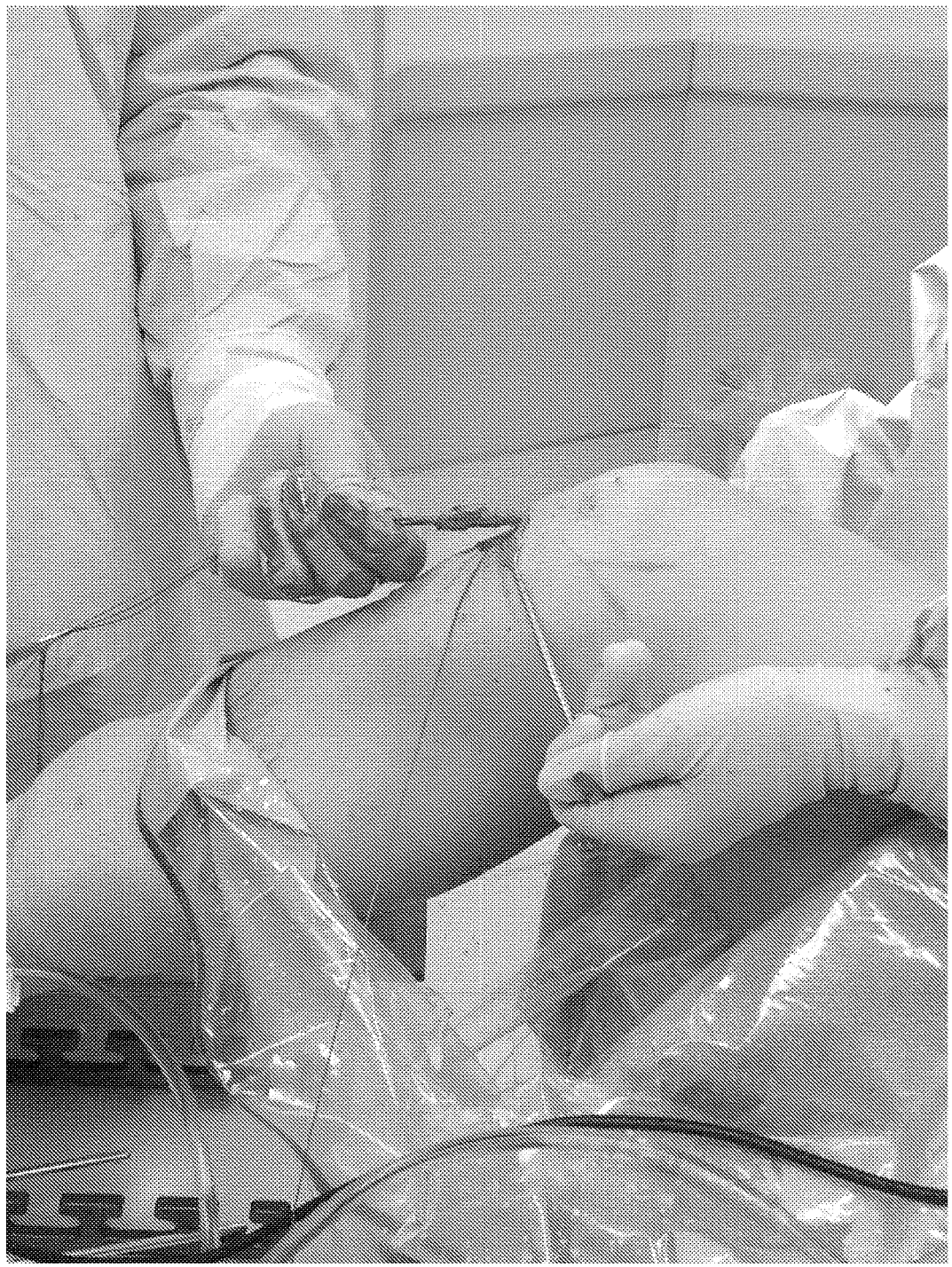
Figure 39:
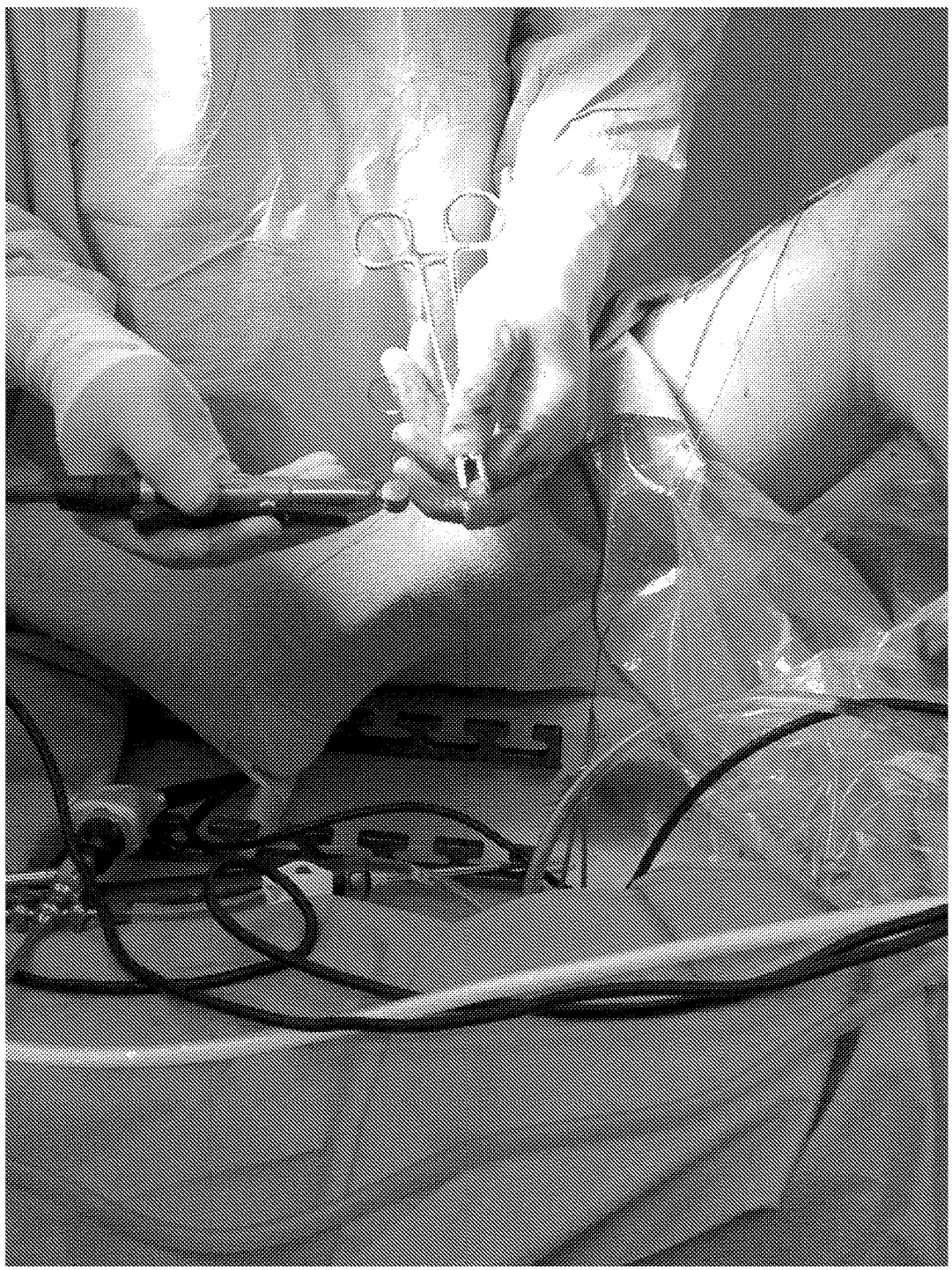
Figure 40:
Figure 41:
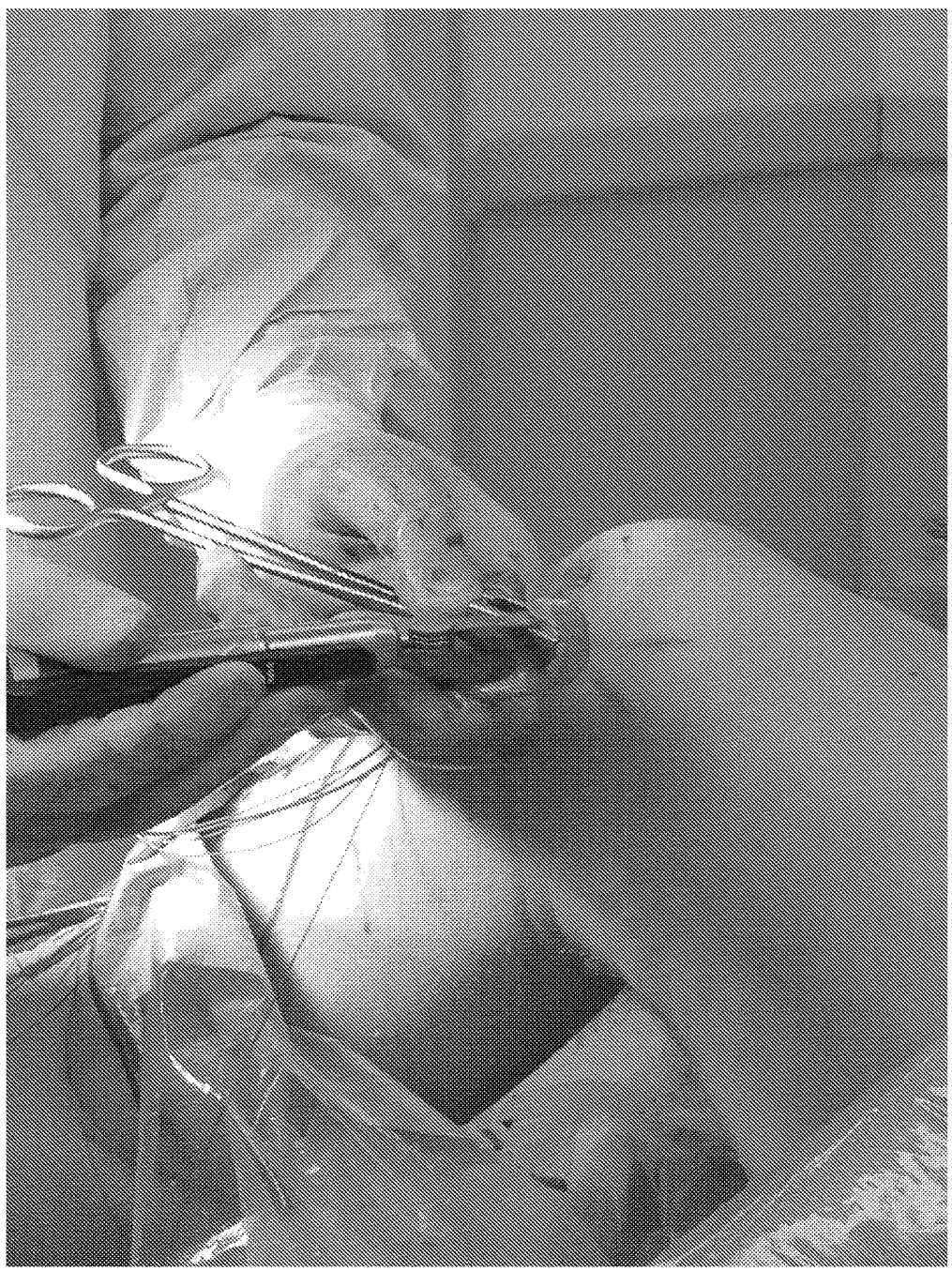
Figure 42:
Figure 43:
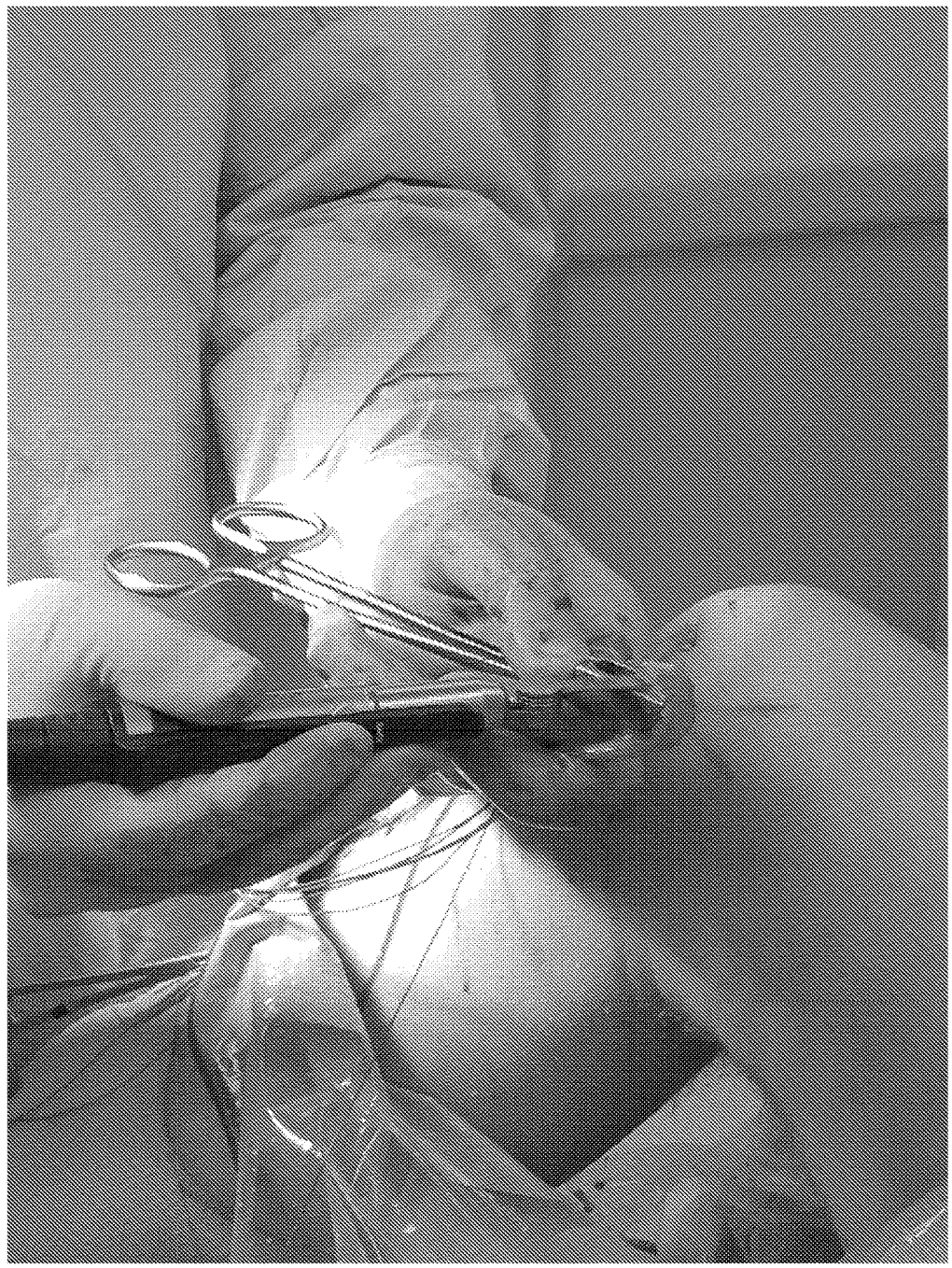
Figure 44:
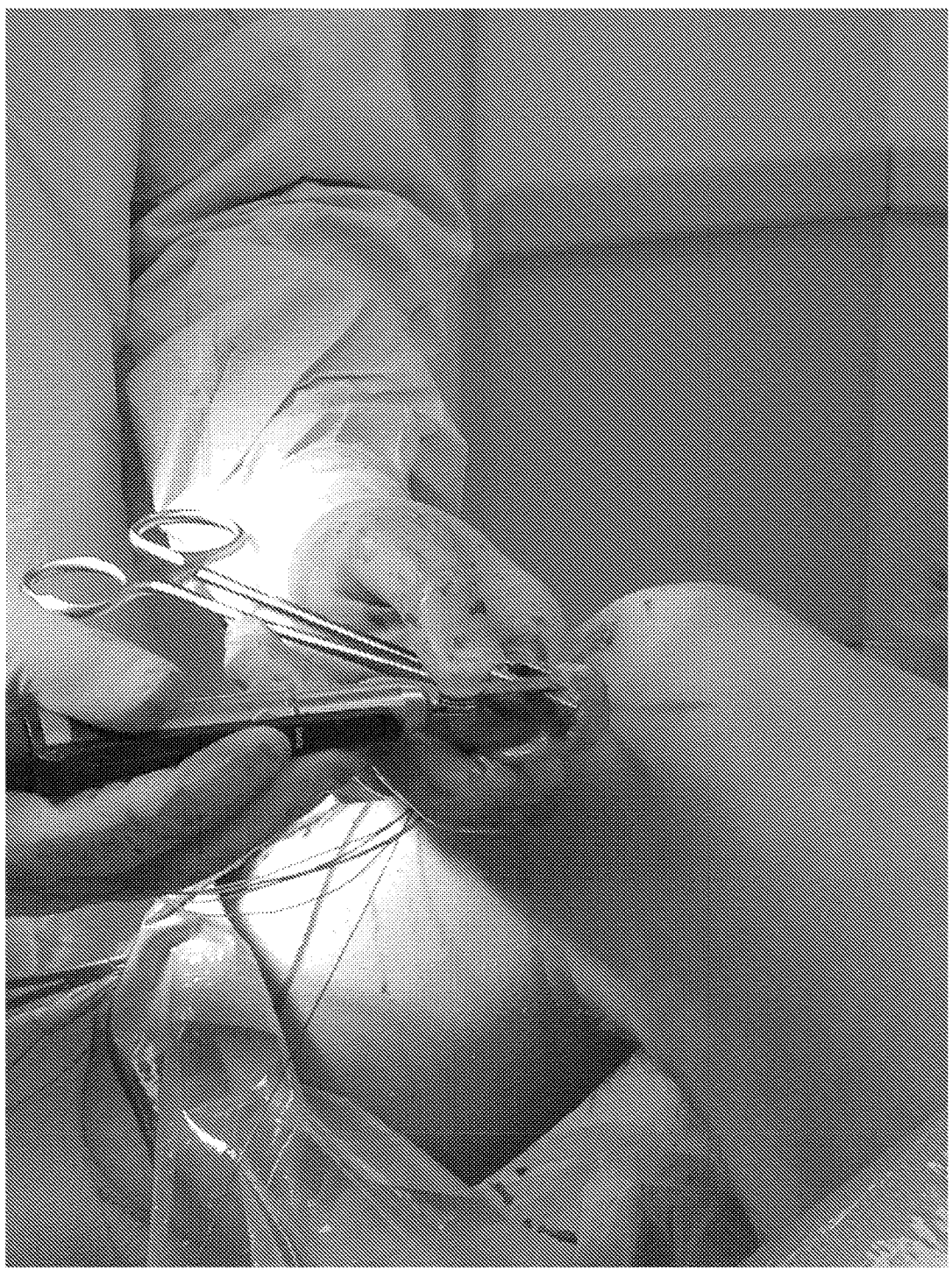
Figure 45:
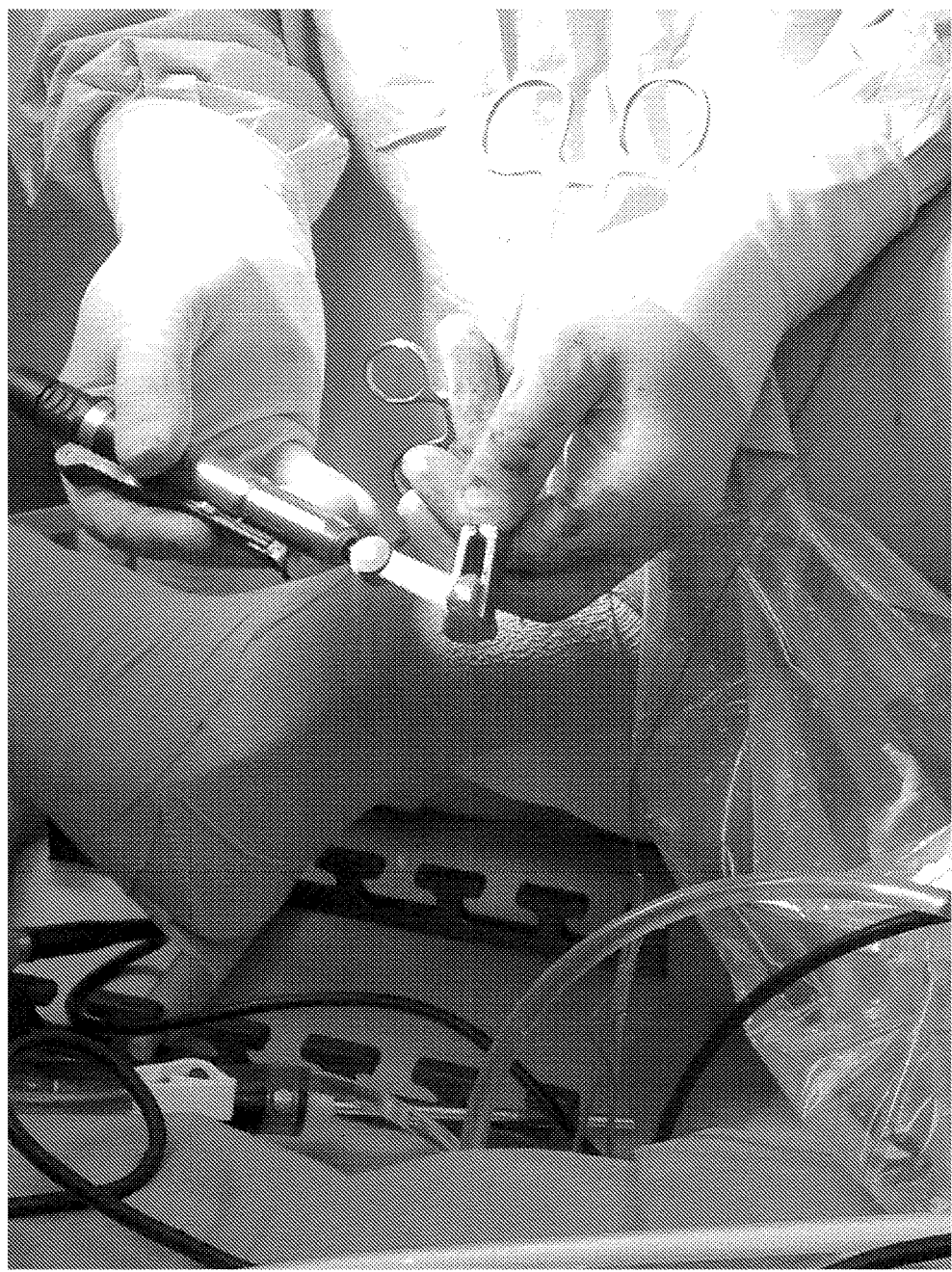
Figure 46:
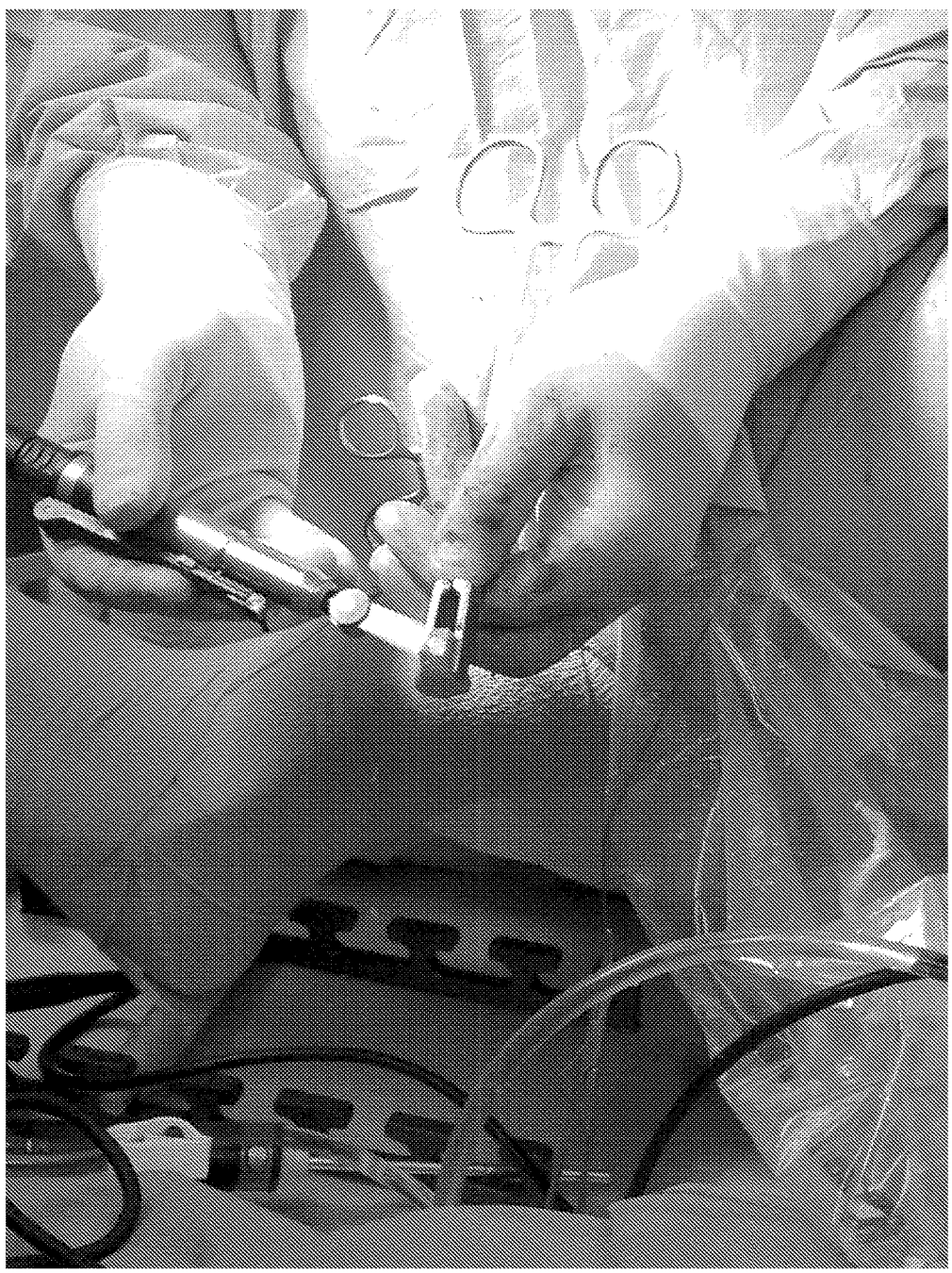
Figure 47:
Figure 48:
Figure 49:
Figure 50:
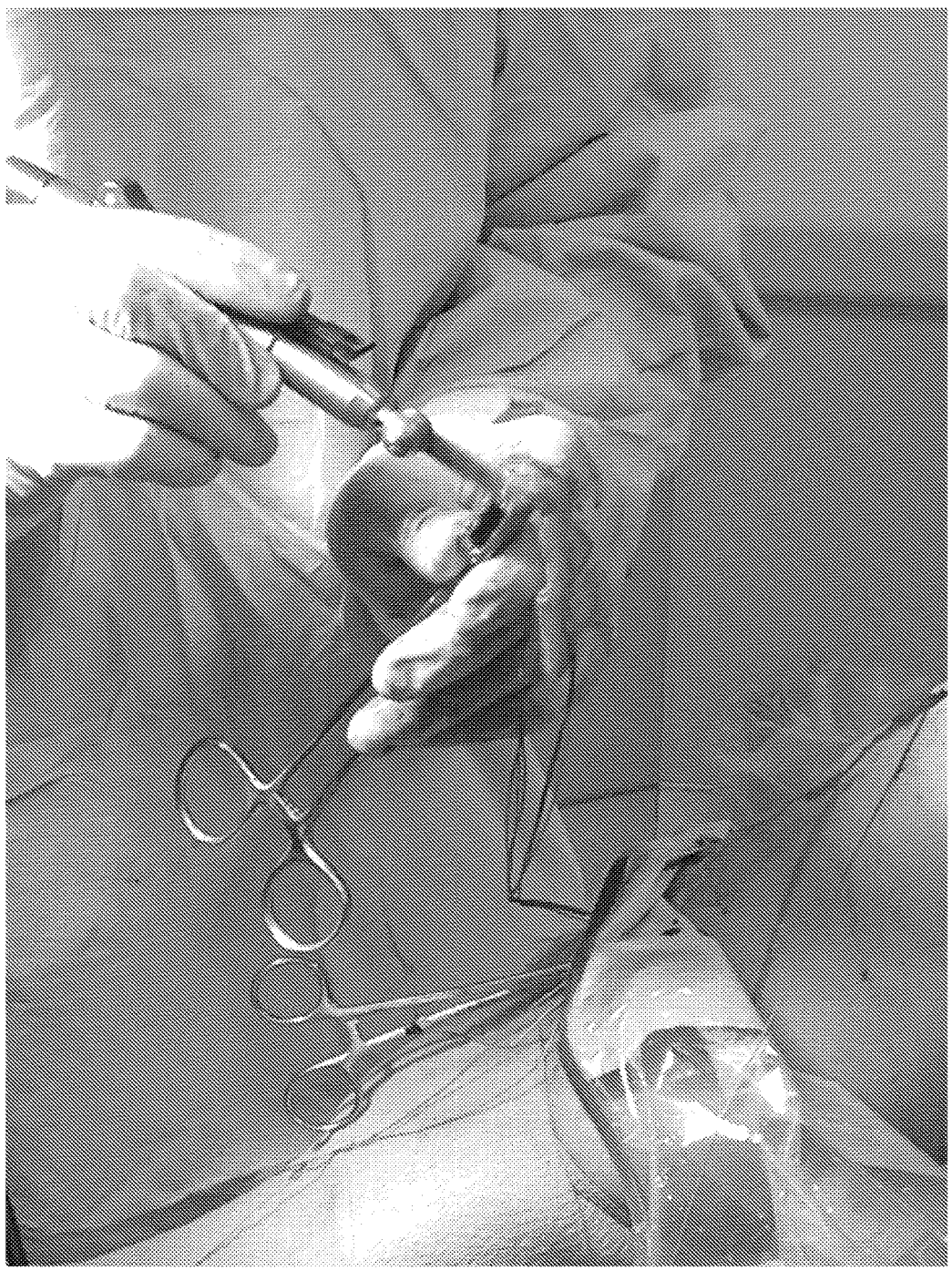
Figure 51:
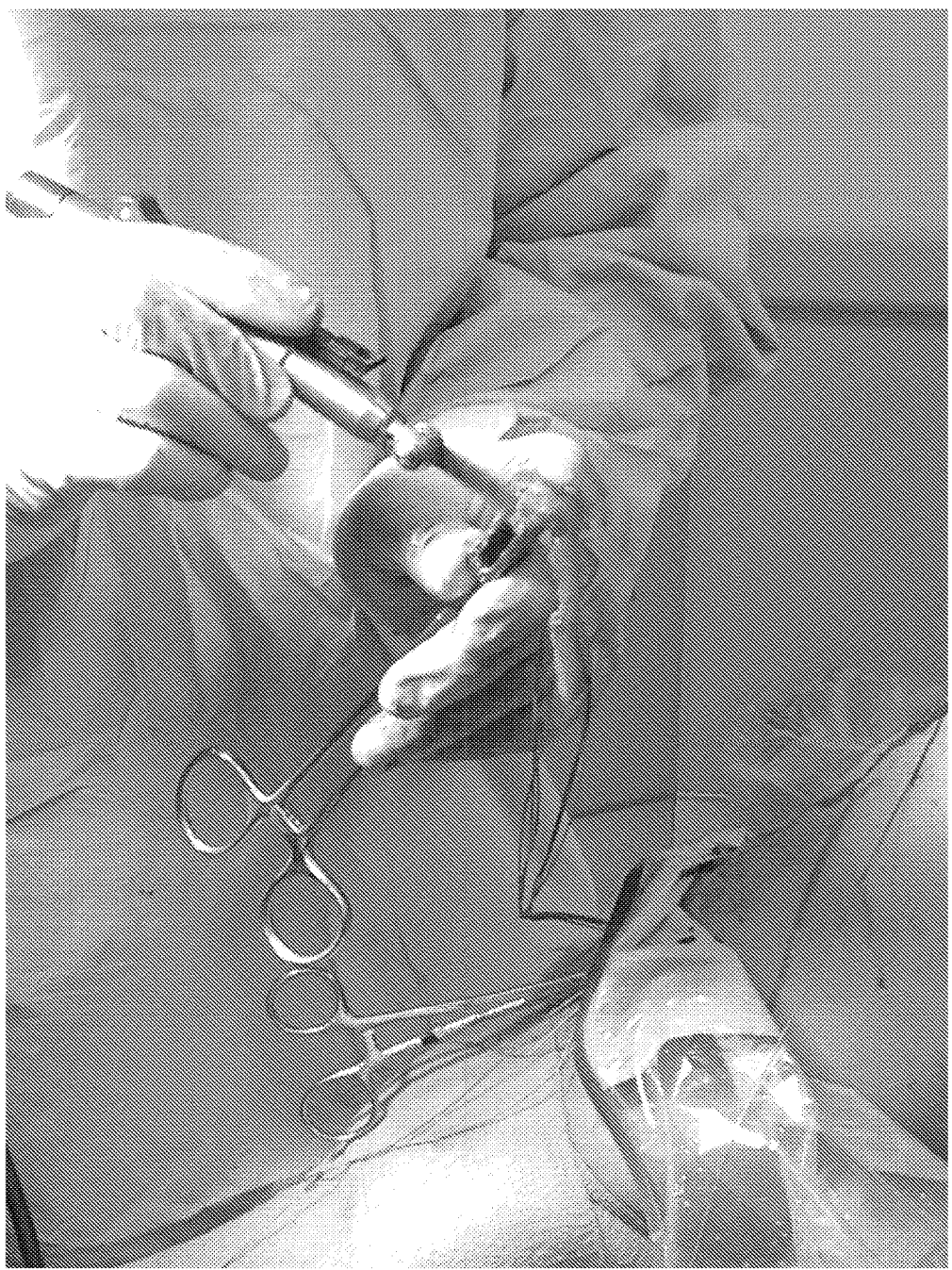
Figure 52:
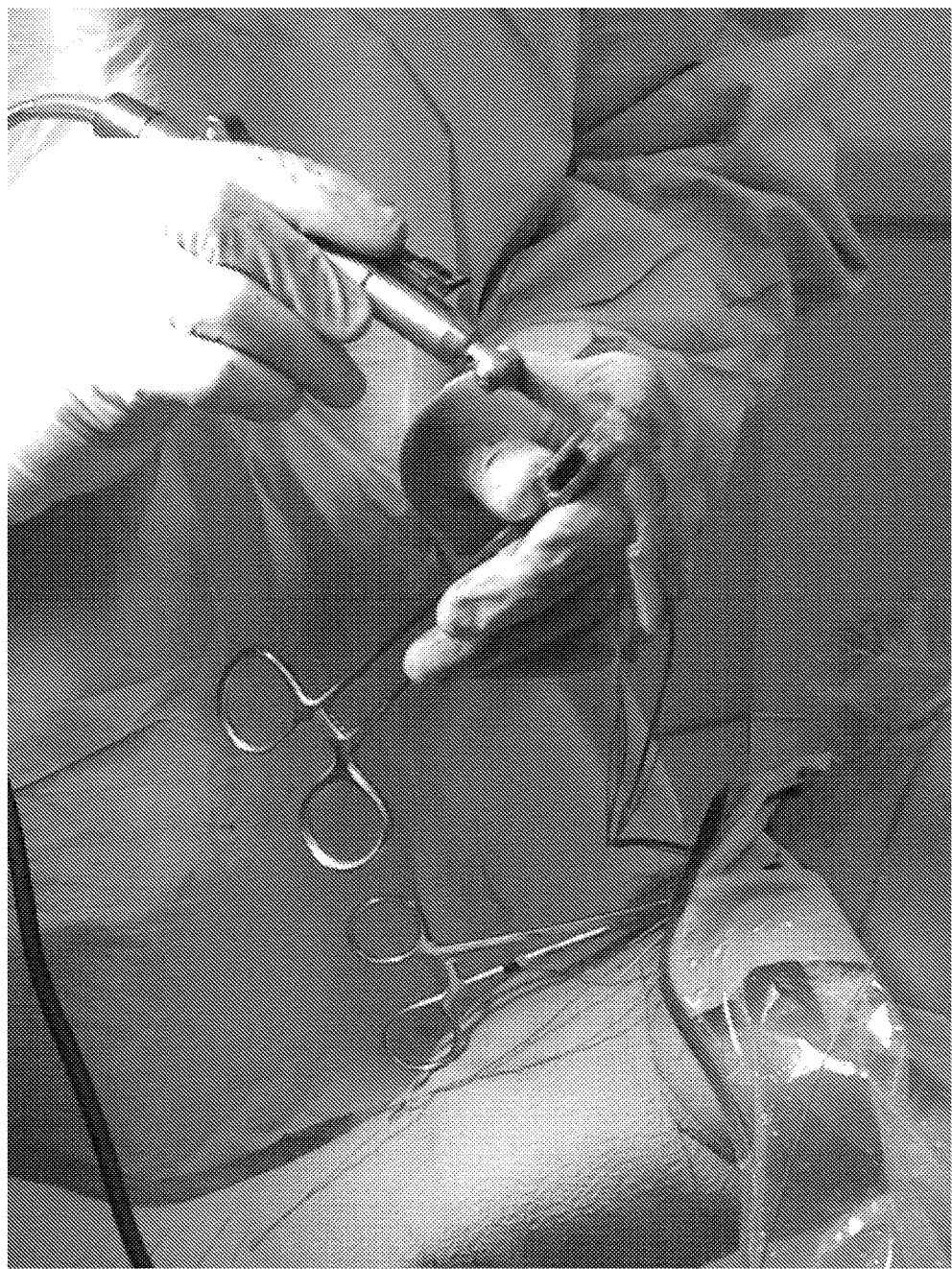
Figure 53:
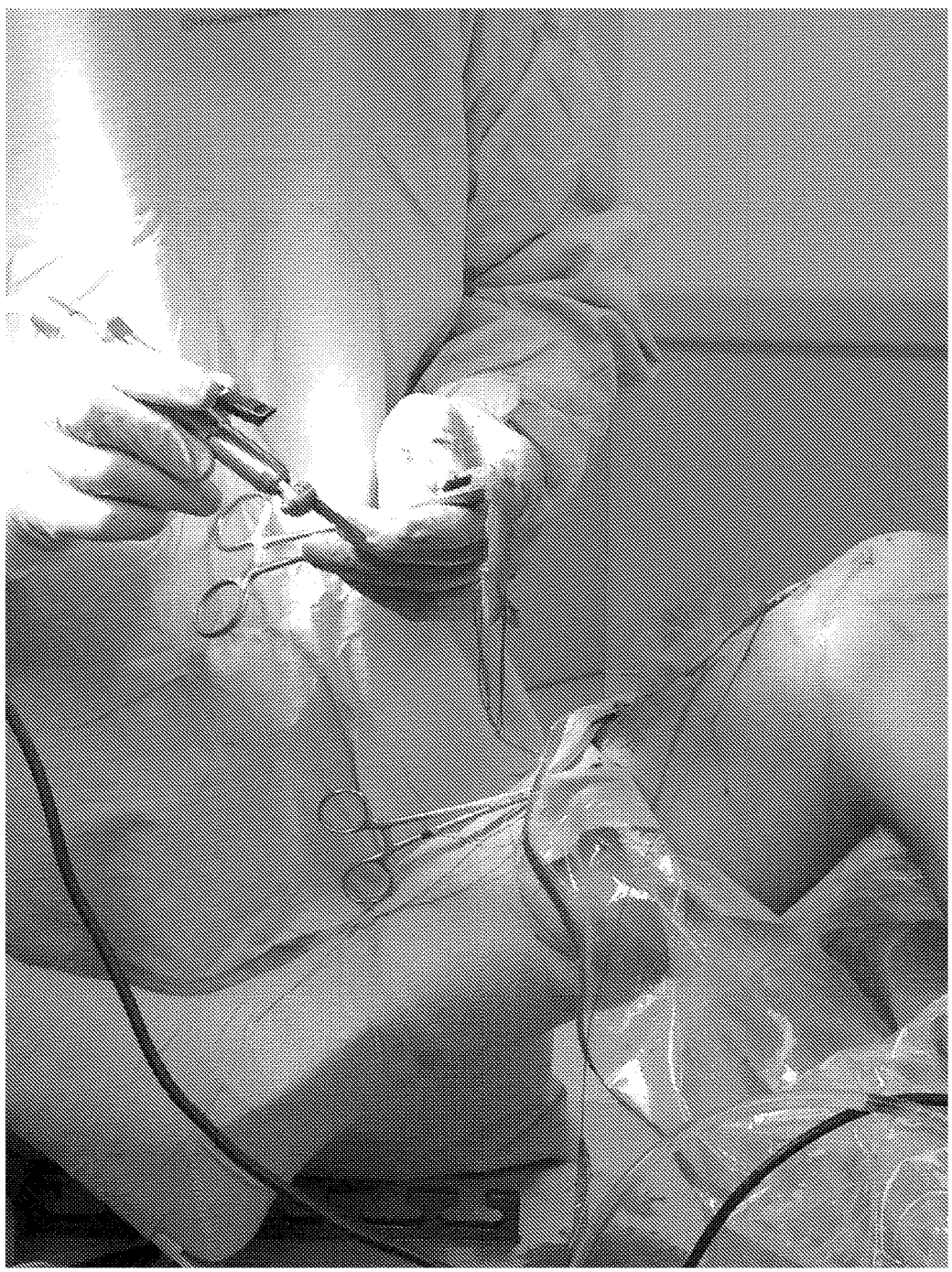
Figure 54:

FIG. 38 shows the inferior portion of the graft secure with sutures.

FIGS. 39 through 53 show the technique being repeated on the patella portion of the graft. The patella portion of the bone is shorter but has the same thickness (e.g., 10 mm). Despite the difference in length, the clamp 10 may be used on either lengths of the bone plugs due to the longer-than-needed length of the generally U-shaped trapezoidal receptacle defined by respective upstanding rear walls 40 and 42.

Figure 55:
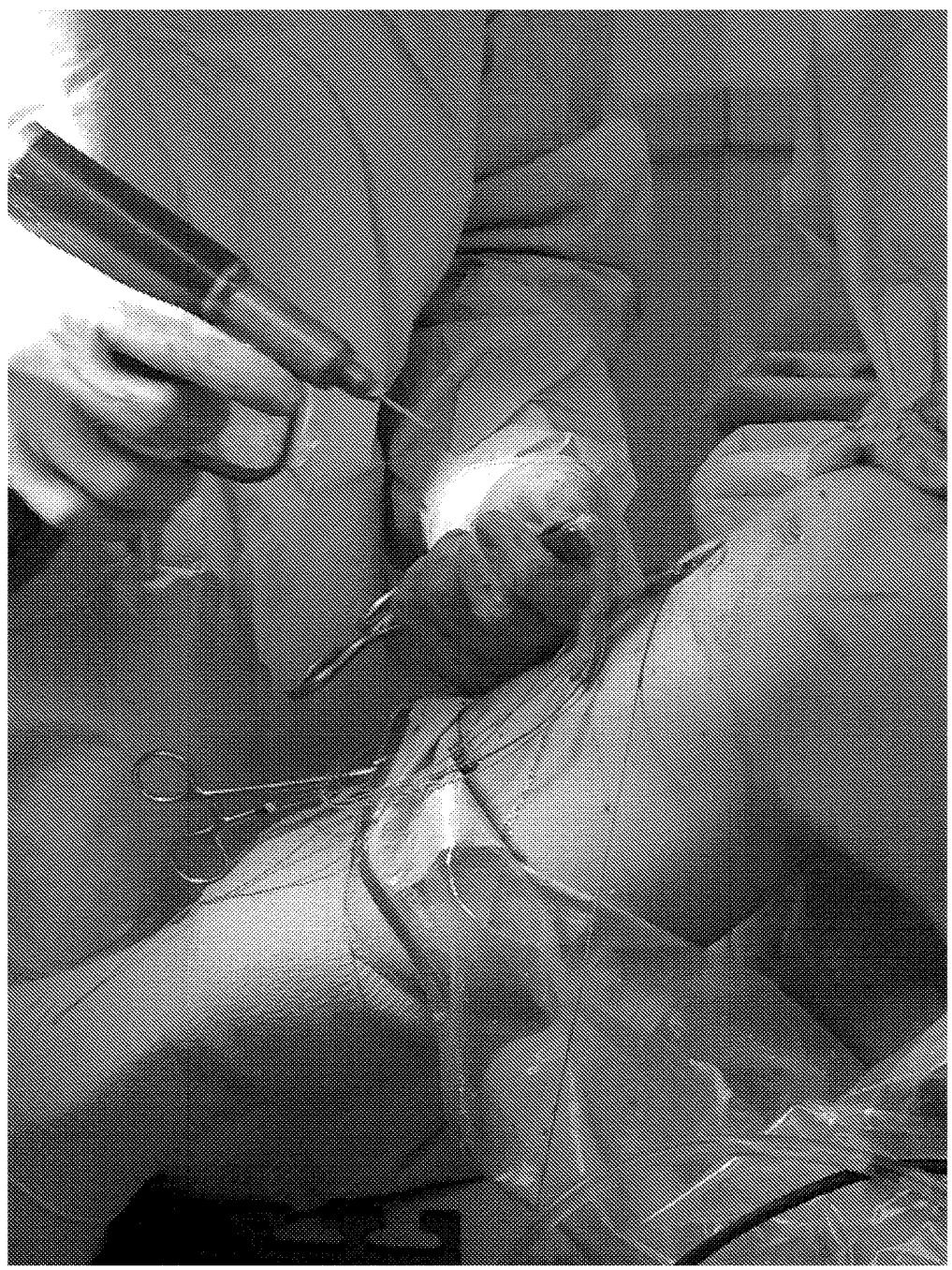

FIGS. 55 and 56 show a drill hole made into the patella portion of the graft and with sutures passed through the patella portion of the graft just as they were passed through on the tibial portion of the graft. Now the graft is prepared to be passed into the knee joint and the patella tendon is turned into the ACL.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A method for clamping and trimming a bone tendon portion of a graft to a desired size, comprising the steps of:
    clamping a pair of jaws the jaws defining a generally U-shaped receptacle about the bone tendon portion of the graft to be trimmed, wherein the jaws comprise respective upstanding, inwardly-sloping sidewalls sloping from a narrower width at a top portion to a wider width at a bottom portion of the jaws to define the generally U-shaped trapezoidal receptacle when the jaws are closed; and
    trimming an excess portion of the bone tendon portion protruding from an upper guide surface of the jaws by moving a cutting instrument along the upper guide surface to trim the excess portion of the bone tendon portion protruding outside the upper guide surface.

2. The method as set forth in claim 1, wherein the generally U-shaped receptacle comprises a generally U-shaped trapezoidal receptacle.

3. The method as set forth in claim 1, further including the step of interconnecting the jaws.

4. The method as set forth in claim 1, wherein the graft comprises repairing anterior cruciate ligament of a human knee.

5. The method as set forth in claim 1, further including the step of, after trimming one side of the bone tendon portion, releasing the bone tendon portion from the jaws, rotating the bone tendon portion about ninety degrees and re-cradling the bone tendon portion within the jaws and then trimming any excess of the bone tendon portion protruding from the upper guide surface by moving a cutting instrument along the upper guide surface.

* * * * *